United States Patent
Zimmermann

(10) Patent No.: US 12,384,412 B2
(45) Date of Patent: Aug. 12, 2025

(54) INFORMATION PROCESSING CIRCUITRY AND INFORMATION PROCESSING METHOD

(71) Applicant: Sony Group Corporation, Tokyo (JP)

(72) Inventor: Klaus Zimmermann, Stuttgart (DE)

(73) Assignee: SONY GROUP CORPORATION, Tokyo (JP)

( * ) Notice: Subject to any disclaimer, the term of this patent is extended or adjusted under 35 U.S.C. 154(b) by 477 days.

(21) Appl. No.: 17/696,893

(22) Filed: Mar. 17, 2022

(65) Prior Publication Data
US 2022/0306155 A1 Sep. 29, 2022

(30) Foreign Application Priority Data
Mar. 25, 2021 (EP) .................................... 21164929

(51) Int. Cl.
*A61B 5/18* (2006.01)
*A61B 5/00* (2006.01)
(Continued)

(52) U.S. Cl.
CPC ....... *B60W 60/0013* (2020.02); *A61B 5/6893* (2013.01); *B60H 3/0035* (2013.01);
(Continued)

(58) Field of Classification Search
CPC ............. B60W 60/0013; B60W 10/30; B60W 2540/221; A61B 5/6893; A61B 2503/12;
(Continued)

(56) References Cited

U.S. PATENT DOCUMENTS

| 2006/0088187 A1 | 4/2006 | Clarkson et al. |
| 2015/0094896 A1 | 4/2015 | Cuddihy et al. |

(Continued)

FOREIGN PATENT DOCUMENTS

| CN | 114912938 A | * 8/2022 | |
| WO | WO-2012100082 A2 | * 7/2012 | ............. A41D 1/002 |

OTHER PUBLICATIONS

Vincent Karas—Audiovisual Affect Recognition for Autonomous Vehicles: Applications and Future Agendas p. 4-9 (Year: 2024).*

*Primary Examiner* — Ilana L Spar
*Assistant Examiner* — Darnell A Pouncil
(74) *Attorney, Agent, or Firm* — XSENSUS LLP

(57) ABSTRACT

An information processing circuitry for controlling a content provided to a user inside a cabin of an autonomous vehicle, wherein the information processing circuitry is configured to:
  obtain environment data;
  acquire abstract content data, representing abstract content, being associated with the obtained environment data;
  measure initial user body data of the user and determine, based on the measured initial user body data, an initial emotional state of the user;
  determine and provide a first content, being associated with the abstract content, to the user;
  measure, in response to providing the first content to the user, first user body data of the user and determine, based on the measured first user body data, a first emotional state of the user; and
  if the initial emotional state and the first emotional state of the user are different:
    acquire user content data from a database, representing user content associated with a past user experience,
(Continued)

being associated with the environment data, wherein the user content is associated with the first content, determine, based on a difference between the initial emotional state and the first emotional state of the user, a second content being associated with the user content and being associated with the first content, provide the second content to the user, measure, in response to providing the second content to the user, second user body data of the user and determine, based on the measured second user body data, a second emotional state of the user, and refine, based on a difference between the first emotional state and the second emotional and a difference between the initial emotional state and the second emotional state, the second content provided to the user for increasing the difference between the initial emotional state and the second emotional state of the user.

18 Claims, 7 Drawing Sheets

(51) Int. Cl.
*B60H 3/00* (2006.01)
*B60W 10/30* (2006.01)
*B60W 60/00* (2020.01)
*G06F 3/01* (2006.01)

(52) U.S. Cl.
CPC .............. *B60W 10/30* (2013.01); *G06F 3/015* (2013.01); *A61B 2503/12* (2013.01); *B60W 2540/221* (2020.02)

(58) Field of Classification Search
CPC ......... A61B 5/0022; A61B 5/01; A61B 5/021; A61B 5/024; A61B 5/0816; A61B 5/1128; A61B 5/369; A61B 5/4266; A61B 2503/22; A61B 5/165; A61B 5/18; A61B 5/7267; B60H 3/0035; G06F 3/015; G06F 2203/011

See application file for complete search history.

(56) References Cited

U.S. PATENT DOCUMENTS

| | | |
|---|---|---|
| 2018/0018899 A1 | 1/2018 | Okumura et al. |
| 2019/0034536 A1 | 1/2019 | Papp et al. |
| 2020/0073884 A1 | 3/2020 | Yamada et al. |
| 2020/0138356 A1* | 5/2020 | Sharon .................. A61B 5/0205 |
| 2021/0204023 A1* | 7/2021 | Knox ............... H04N 21/42201 |
| 2024/0001068 A1* | 1/2024 | Wilker .................. A61M 21/02 |

* cited by examiner

INFORMATION PROCESSING CIRCUITRY AND INFORMATION PROCESSING METHOD

CROSS-REFERENCE TO RELATED APPLICATION

The present application claims priority to European Patent Application No. 21164929.8, filed Mar. 25, 2021, the entire contents of which are incorporated herein by reference.

TECHNICAL FIELD

The present disclosure generally pertains to an information processing circuitry for controlling a content provided to a user inside a cabin of an autonomous vehicle and a corresponding information processing method.

TECHNICAL BACKGROUND

In the advent of autonomous vehicles, it is possible that the driver is released from the driving task and becomes a passenger or user of the autonomous vehicle. Some scenarios have already been created indicating a new way of transportation from location A to B in which the passenger(s) may focus on other tasks rather than on driving the vehicle. A computer may completely control the driving in the most advanced level of autonomous driving.

In such scenarios, the question arises about what particular tasks the passenger(s) or user(s) may focus on, and, for example, the vehicle may become a workplace allowing the passenger to efficiently perform his professional work inside the autonomous vehicle or the autonomous vehicle may be used as a place for relaxation, etc. Another use case of autonomous vehicles may be entertainment.

In recent years, more entertainment opportunities have been added to the interior of a vehicle for entertaining passengers during a ride, for example, display devices for playing a movie and audio devices for playing music or the like.

Moreover, network connectivity in cities and in remote areas is increasing rapidly and may allow, for example, a constant access to the internet which may be used to stream, e.g., video and audio content on-demand for entertainment of the passengers in the autonomous vehicle.

Although there exist techniques for providing content in an autonomous vehicle, it is generally desirable to improve the existing techniques.

SUMMARY

According to a first aspect the disclosure provides an information processing circuitry for controlling a content provided to a user inside a cabin of an autonomous vehicle, wherein the information processing circuitry is configured to:
  obtain environment data;
  acquire abstract content data, representing abstract content, being associated with the obtained environment data;
  measure initial user body data of the user and determine, based on the measured initial user body data, an initial emotional state of the user; determine and provide a first content, being associated with the abstract content, to the user;
  measure, in response to providing the first content to the user, first user body data of the user and determine, based on the measured first user body data, a first emotional state of the user; and
  if the initial emotional state and the first emotional state of the user are different:
    acquire user content data from a database, representing user content associated with a past user experience, being associated with the environment data, wherein the user content is associated with the first content,
    determine, based on a difference between the initial emotional state and the first emotional state of the user, a second content being associated with the user content and being associated with the first content,
    provide the second content to the user,
    measure, in response to providing the second content to the user, second user body data of the user and determine, based on the measured second user body data, a second emotional state of the user, and
    refine, based on a difference between the first emotional state and the second emotional and a difference between the initial emotional state and the second emotional state, the second content provided to the user for increasing the difference between the initial emotional state and the second emotional state of the user.

According to a second aspect the disclosure provides an information processing method for controlling a content provided to a user inside a cabin of an autonomous vehicle, comprising:
  obtaining environment data;
  acquiring abstract content data, representing abstract content, being associated with the obtained environment data;
  measuring initial user body data of the user and determining, based on the measured initial user body data, an initial emotional state of the user;
  determining and providing a first content, being associated with the abstract content, to the user;
  measuring, in response to providing the first content to the user, first user body data of the user and determining, based on the measured first user body data, a first emotional state of the user; and
  if the initial emotional state and the first emotional state of the user are different:
    acquiring user content data from a database, representing user content associated with a past user experience, being associated with the environment data, wherein the user content is associated with the first content,
    determining, based on a difference between the initial emotional state and the first emotional state of the user, a second content being associated with the user content and being associated with the first content,
    providing the second content to the user,
    measuring, in response to providing the second content to the user, second user body data of the user and determine, based on the measured second user body data, a second emotional state of the user, and
    refining, based on a difference between the first emotional state and the second emotional and a difference between the initial emotional state and the second emotional state, the second content provided to the user for increasing the difference between the initial emotional state and the second emotional state of the user.

Further aspects are set forth in the dependent claims, the following description and the drawings.

BRIEF DESCRIPTION OF THE DRAWINGS

Embodiments are explained by way of example with respect to the accompanying drawings, in which.

DETAILED DESCRIPTION OF EMBODIMENTS

Figure 1:
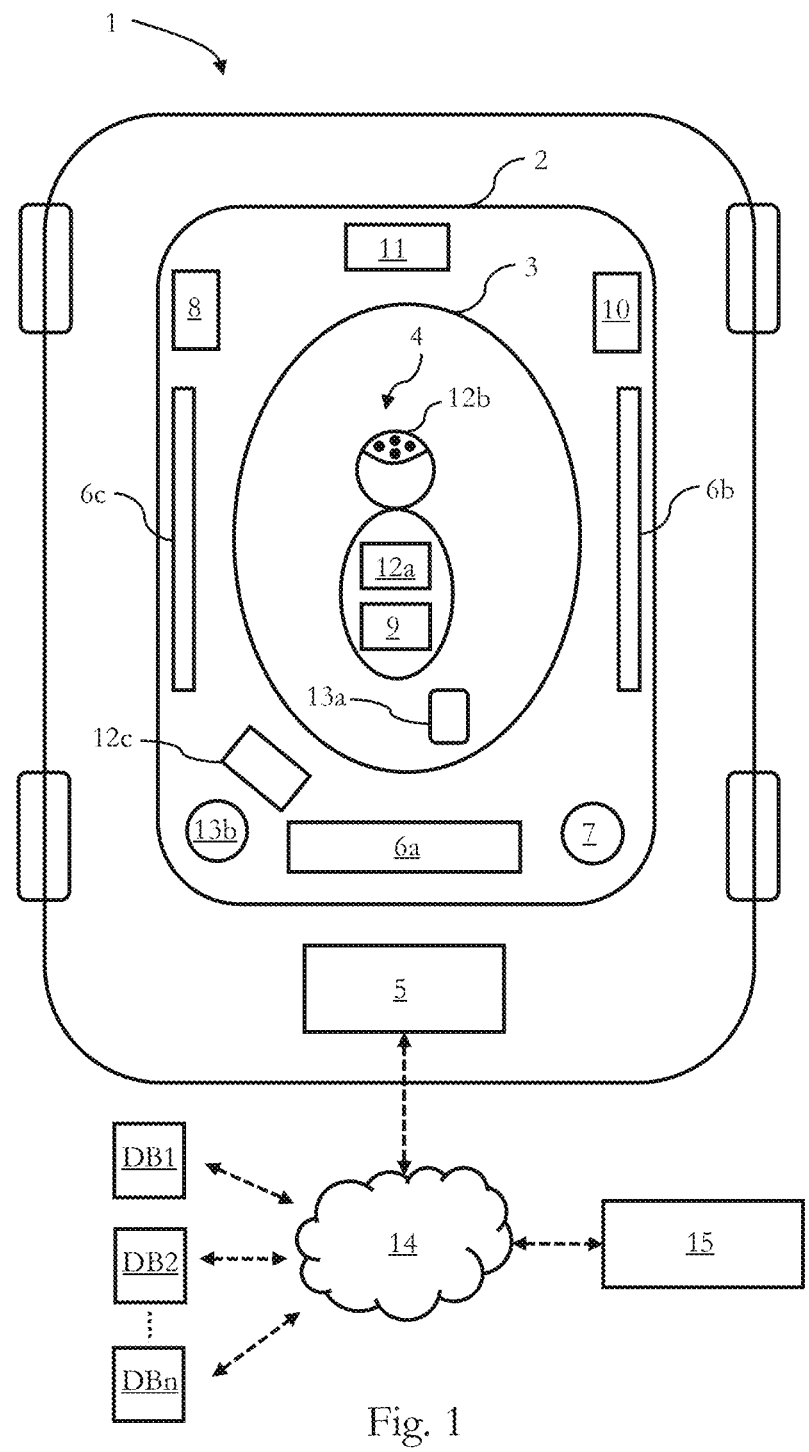
FIG. 1 schematically illustrates in a block diagram an embodiment of an autonomous vehicle including.

Before a detailed description of the embodiments under reference of FIG. 1 is given, general explanations are made.

In recent years, more entertainment opportunities have been added to the interior of a vehicle for entertaining passengers during a ride, for example, display devices for playing a movie and audio devices for playing music or the like. In autonomous vehicles the number of entertainment opportunities may increase, since, for example, the interior of the autonomous vehicle may be completely redesigned as a steering wheel may not be required anymore and the passengers may focus on other tasks than driving such as entertainment.

Moreover, network connectivity in cities and in remote areas is increasing rapidly and may allow, for example, a constant access to the internet which may be used to stream, e.g., video and audio content on-demand for entertainment of the passengers in the autonomous vehicle.

It has been recognized that this may allow a user (passenger) in an autonomous vehicle, for example, to view images and videos the user has taken in the past and recall experiences.

Generally, a service is known which provides the user with images taken a year ago, for example, on the user's smartphone in order to remind the user of what has happened in the user's life at the same time the year ago. Accordingly, the user is triggered to recall an experience based on a particular date and the image as a visual impression.

However, it has been recognized that a reminiscence of a past event may be based on further impressions such as music, verbal communication, smells, touches experienced with the user's senses at that past event.

Moreover, it has been recognized that a user may not be consciously aware of a particular memory or reminiscence, but the user may be able to recall experiences if the user is actively triggered in particular situation by providing different sort of content to the user which is associated with the particular situation.

For example, when the user is sitting in the autonomous vehicle which drives by a location the user has been before or drives through a geographical area or landscape similar to where the user used to live or used to spend holidays, the user may be triggered to recall the user's experiences (reminiscence, memory of the user) by providing content to the user which is associated with the location or geographical area (e.g. ocean sounds).

Moreover, it has been recognized that this content may be further refined by content of the user (e.g. content from the user's account stored on a database of a social network server) in order to actively increase an emotional response to the content in order to enhance the recall of the experience when driving in the autonomous vehicle. Additionally, artificial computer-generated content may be provided to the user which is associated with the user content for enhancing an emotional response of the user.

Generally, the content provided to the user may address all senses of the user individually or in an arbitrary composition. This may allow a user to travel back in time by exposing the user to previous experiences inside the autonomous vehicle triggered by the content provided to the user.

Hence, some embodiments pertain to an information processing circuitry for controlling a content provided to a user inside a cabin of an autonomous vehicle, wherein the information processing circuitry is configured to:
obtain environment data;
acquire abstract content data, representing abstract content, being associated with the obtained environment data;
measure initial user body data of the user and determine, based on the measured initial user body data, an initial emotional state of the user;
determine and provide a first content, being associated with the abstract content, to the user;
measure, in response to providing the first content to the user, first user body data of the user and determine, based on the measured first user body data, a first emotional state of the user; and
if the initial emotional state and the first emotional state of the user are different:
acquire user content data from a database, representing user content associated with a past user experience, being associated with the environment data, wherein the user content is associated with the first content,
determine, based on a difference between the initial emotional state and the first emotional state of the user, a second content being associated with the user content and being associated with the first content,
provide the second content to the user,
measure, in response to providing the second content to the user, second user body data of the user and determine, based on the measured second user body data, a second emotional state of the user, and
refine, based on a difference between the first emotional state and the second emotional and a difference between the initial emotional state and the second emotional state, the second content provided to the user for increasing the difference between the initial emotional state and the second emotional state of the user.

The information processing circuitry (or information processing system) is included or part of an autonomous vehicle (in the following abbreviated with vehicle) which is a car driving, e.g. completely controlled by a computer.

The information processing circuitry (or information processing system) may be based on or may include or may be implemented by typical electronic components configured to achieve the functionality as described herein.

The information processing circuitry may be based on or may include or may be implemented as integrated circuity logic and the functionality may be implemented by software executed by a processor or the like. The information processing circuitry may be based on or may include or may be implemented by a CPU (central processing unit), a microcontroller, an FPGA (field programmable gate array), an ASIC (application specific integrated circuit) or the like.

The information processing circuitry may be based on or may include or may be implemented in parts by typical electronic components and integrated circuitry logic and in parts by software.

The information processing circuitry may include a communication interface configured to communicate and exchange data with a network (e.g. the internet) and computer(s) in the network over a wireless connection such as a mobile telecommunications system which may be based on UMTS, LTE or the like (and implements corresponding communication protocols). The information processing circuitry may also include data storage capabilities to store data.

The content may be visual content (e.g. text, images, videos or computer-generated visual sequences displayed on a display device, light conditions of light elements (e.g. lamps, LED tubes, etc.), and the like) to trigger a visual impression of the user inside the cabin of the vehicle, audio content (e.g. music, voices, sound elements, and the like) to trigger an audio impression of the user, smell content (e.g. released aromas) to trigger a smell impression of the user, touch content (e.g. electrical signals provided) to trigger a touch impression of the user, taste content (e.g. providing a coffee) to trigger a taste impression of the user, temperature content (e.g. heating or cooling) to trigger a temperature impression of the user, and the like or other types of haptic or sensual contents.

In some embodiments, the information processing circuitry provides visual content inside the cabin to the user as part of the provided content. In such embodiments, the information processing circuitry includes display devices, light elements, and the like to provide the visual content to the user (visual content providing unit).

In some embodiments, the information processing circuitry provides audio content inside the cabin to the user as part of the provided content. The audio content may be music, verbal communication, sounds, and the like. In such embodiments, the information processing circuitry includes a speaker and the like to provide the audio content to the user (audio content providing units).

In some embodiments, the information processing circuitry provides smell content inside the cabin to the user as part of the provided content. In such embodiments, a smell content providing unit includes a plurality of containers including substances, e.g., gases and liquids having a particular smell such as aromas or the like. In such embodiments, the information processing circuitry is configured to control a release of the substances in the cabin to provide the smell content to the user (smell content providing unit). For example, a plurality of predetermined liquids may be provided such as salted water which may simulate/provide an "ocean smell" to the user, or a coffee or tea aroma which may simulate/provide a "coffee/tea store smell" to the user, or a parfum, or an aroma of a particular flower, or the like.

In some embodiments, the information processing circuitry provides haptic content to the user as part of the provided content. In such embodiments, the information processing circuitry includes wearables (e.g, a glove or a vest) attached to the user's body including, e.g., (small) electrodes which provide an electric signal to the skin of the user, thereby a simulated sense of touch may be provided. In such embodiments, the information processing circuitry controls the electric signals provided through the electrodes to the skin of the user to provide the haptic content to the user (haptic content providing unit).

The information processing circuitry (or information processing system) obtains environment data.

The environment data representing environment information may be location data of the vehicle (representing positional information of the vehicle), object data representing object information about objects in the vicinity of the vehicle (e.g. representing a kind of an object such as a tree, a coffee store, a building, etc. the vehicle drives by) or in a predetermined distance to the location of the vehicle (e.g. in a 5 km, 10 km, . . . radius), area data representing area information about places, landscapes, attractions, etc. in a predetermined distance to the location of the vehicle, and the like. The environment data may further be display data representing display information of a display device inside the vehicle, sound data representing sound information inside and/or outside the vehicle, smell data (e.g. representing odors or flavors or particles in the air) representing smell information inside and/or outside the vehicle, and the like.

The environment data may be obtained from a positioning sensor (e.g, a GPS sensor) in the vehicle, cameras mounted in the vehicle imaging the surrounding of the vehicle, depth sensors in the vehicle generating depth information of the surrounding of the vehicle, a detailed (digital) map, and the like. The environment data may further be obtained from a display device for obtaining display data (e.g. the user may watch a video), an electronic nose detecting odors or flavors in the vicinity of the vehicle or inside the cabin of the vehicle (e.g. smell of a flower) or a particle sensor for obtaining smell data, a microphone collecting sound data in the vicinity of the vehicle (e.g. sound of a church bell, an ocean, etc.) or inside the cabin of the vehicle (e.g. verbal communication of the user, music played back, etc.), and the like. Moreover, the environment data may be obtained via a network, e.g. including the internet, and may be provided from another electronic device (e.g. smartphone, laptop, etc.), from environment data providing services including remote (cloud) based computer systems etc.

Accordingly, the environment data may represent information about a particular situation, location and area (e.g. scenery driven by, music played back, verbal communication, etc.) inside and outside the vehicle.

The information processing circuitry acquires abstract content data, representing abstract content, being associated with the obtained environment data.

The abstract content may be visual content, audio content, smell content, and the like. The abstract content is or includes a first level of content (which may have a low degree of detailedness) which is used as a trigger (cue) to stimulate an emotional reaction of the user (which may be due to triggering an experience).

The abstract content may be acquired from a search engine. For instance, the information processing circuitry may generate a search command including at least a part of the environment information and the search command is transmitted via a network to a server of the search engine and the searched information (abstract content) is transmitted back to the vehicle and received by the information processing circuitry which stores the acquired abstract content.

The abstract content may (further) be acquired from a server associated with a provider of the vehicle functionality (e.g, a manufacturer of the vehicle providing content on a server for the functionality described herein). For example, the user may have an account or a contract with the provider about providing abstract content on-demand. The provider may have a database storing predetermined content data such as information about a number of predetermined smells (e.g. how a predetermined smell may be generated by releasing a certain amount of predetermined liquids or gases or the like) or information about how to generate a number of predetermined touch feelings (e.g. how a touch feeling is generated by providing electric signals to the skin of the user) or a number of predetermined sounds which may be retrieved from the server of the provider or the like.

The abstract content is associated with the obtained environment information. The term "associated" may refer to a content-related link between the environment information and the abstract content.

For example, when the vehicle drives by a museum and obtains this as an environment information, the abstract content may be, e.g., images of paintings or sculptures or historic artefacts or the like. For example, when the vehicle drives near an ocean side, the abstract content may be images of an ocean and a beach (visual content), sounds of ocean waves (audio content), an ocean smell (smell content), a feeling of sand (touch content), or the like. For example, when the vehicle drives in a city with a sports arena, the abstract content may be images or videos of past sports events, sounds of fans in the sports arena or an anthem of a local sports club, a smell of food typically served in the sports arena or typically served at a sports event, or the like.

The information processing circuitry measures initial user body data of the user and determines, based on the measured initial user body data, an initial emotional state of the user.

The measured (initial) user body data may include a heart rate of the user, a blood pressure of the user, a body temperature of the user, a respiration rate of the user, an amount of sweat of the user, hormone values of the user, gestures and mimics of the user (e.g. smiling, crying, yawning, etc.), electric signals of the user's brain, and the like.

In some embodiments, the information processing circuitry includes a body sensor unit configured to measure the user body data, wherein the user body sensor unit includes at least one of a heart rate sensor, a blood pressure sensor, a body temperature sensor, a respiration rate sensor, a sweat sensor, a hormone sensor and the like attached to the user, and a camera monitoring the user.

In some embodiments, the body sensor unit includes a brain-machine-interface attached to the user. In such embodiments, the brain-machine-interface measures electric signals in several regions of the brain of the user or the brain activity in several regions of the brain, for example, brain activity in a region which is associated with the user's memory. This may allow to determine if the user recalls an experience or the like.

As generally known, such data (user body data) is indicative for an emotional reaction/state of the user. The (initial) emotional state(s) of the user may be classified into a predetermined number of emotional states based on the values of the (physiological) parameters and the mimics and gestures. The predetermined number of emotional states may be ordered based on, for example, a deviation to typical values of the user body data (e.g. ordered according to an excitement or the like). The initial emotional state may be a determined reference when the user is not actively (automatically) provided with content. The initial emotional state is used as a reference to determine an emotional reaction of the user in response to provided content.

The information processing circuitry determines and provides a first content, which is associated with the abstract content, to the user.

The first content may be visual content, audio content, smell content, or the like. The first content may be randomly selected (determined) from the acquired abstract content to provide a trigger to the user for recalling an experience or the like.

The first content may be computer-generated content (the information processing circuitry may be configured to generate artificial content, e.g., artificial images, music, and the like), which is generated (determined) based on the acquired abstract content and which is associated with the abstract content. For example, the acquired abstract content may include an image of church driven by or located in the city the vehicle is driving, the image processing circuitry may analyze the objects shown in the image (object detection and classification in images is generally known) and may generate an artificial sound of a church bell provided to the user.

The first content is provided to the user according to its content type, for example, images or videos (visual content) are displayed (provided) to the user on a screen, music or sounds (audio content) are played back (provided) to the user by a speaker, etc.

The information processing circuitry measures, in response to providing the first content to the user, first user body data of the user and determines, based on the measured first user body data, a first emotional state of the user.

The first user body data may be measured a predetermined time after providing the first content (e.g. 10 seconds or 20 seconds without limiting the disclosure in this regard and the time period may be adapted to the specific embodiment, to the particularities of the user, to user adjustments, inputs, or the like), which is intended to trigger an emotional reaction, for example, due to triggering a recall of a user's past experience. The first emotional state is determined based on the first user body data as discussed for the initial emotional state.

Based on a determined change of the emotional state (e.g. due to an emotional reaction to the provided first content), it may be determined whether such first content provided to the user is suitable to enhance or influence the emotional state of the user.

If the initial emotional state and the first emotional state of the user are different, it may be likely that the user has made experiences associated with the first content. In some embodiments, the difference is compared, for example, with a threshold in order to determine whether the difference is large enough in order to determine whether the change of the emotional state is large enough. In some embodiments, the difference is further analyzed in order to determine whether the change of the emotional state can be associated with predefined emotional states, e.g. upset, happy, sad, etc.

Hence, if the initial emotional state and the first emotional state of the user are different (or additionally, as mentioned, if the difference complies with further criteria, such as exceeding threshold, meeting a target emotional state or the like), the information processing circuitry acquires user content data from a database, representing user content associated with a past user experience, being associated with the environment data, and wherein the user content is associated with the first content.

The database may be a database of a social networking server (the user may have an account on the corresponding social network), a database of a video content provider (the user may have an account on the corresponding video content platform), a database of a messenger application the user is using, a database of a provider of smart home devices (e.g. of a smart speaker which the user uses in the user's home), a database of a provider of (sport) wearable devices (e.g, a smart watch of the user to acquire activity information), a database of a music application provider (e.g. to acquire information about songs the user listened to in the past), a database of a financial service provider or online retail store (e.g. to acquire information about purchases the user made), and the like.

As discussed above for the abstract content, the user may have an account with the provider of the vehicle functionality and the provider may have the permission to query certain databases on which user content data is stored and store the respective user content data on its own server such that the user content may be acquired from a database of the provider. The database may also be a database of this provider in which information of previous rides and provided content is stored.

Generally, the user may give permission to access certain databases to query user content stored in these databases, e.g., the user may give permission to access the user's account on a social network.

The user content may be visual content, audio content, smell content, and the like. The user content is a second level of content (which may have a higher degree of detailedness than the abstract/first content) which is used as a trigger (cue) to stimulate an emotional reaction of the user due to the past experience of the user associated with the user content.

The user content data is associated with the environment data and, thus, the user content is associated with the environment information and the user content is associated with the first content. The term "associated" may refer to a content-related link between the environment information, the first content and the user content.

For example, when the user drives in a city with a sports arena (environment information), the first content may be an image or video (or animation in case of a computer-generated first content based on the abstract content) of a previous sports event (e.g, a football game which may took place in that sports arena). In such example, the user content may be a video, image or sound recording (e.g. which the user has taken with the user's smartphone) at a related sports event, e.g., another football game the user visited in that sports arena and, thus, the user content is associated with the environment information and the first content.

The information processing circuitry determines, based on a difference between the initial emotional state and the first emotional state of the user (wherein the difference may be further analyzed as discussed above), a second content being associated with the user content and being associated with the first content.

The second content may be visual content, audio content, smell content, or the like. The second content may be randomly selected (determined) from the acquired user content (and the abstract content) to provide a trigger to the user for recalling an experience and to refine the user experience. The second content (associated with the user content and the first content) may be determined based on a classification of content, e.g., by unsupervised learning strategies or the like (this may allow, for example, to determine an association (content-related link) between abstract and user content).

As for the first content, the second content may be computer-generated content, which may be generated (determined) based on the user content data and abstract content acquired from the database. For example, the computer-generated content may supplement missing pieces in the acquired user content data or enrich the acquired user content data.

Generally, the second content may include the first content with more details added to the content (e.g, added from the user content or generated based on the user content) which is associated with the first content and the user content. The second content may include a more concrete content associated with the first content and the user content, for example, content associated with a concrete activity of the user (the content itself may not be more detailed, however, the association between user and content may be more concrete). The second content may include a different or more concrete abstraction level, for example, the first content may be loosely associated with the environment information (e.g, an image of a beach) and the second content may be refined by, for example, determining content associated with activities at the beach.

As discussed above, if the initial emotional state and the first emotional state of the user are different (or additionally, as mentioned, if the difference complies with further criteria, such as exceeding threshold, meeting a target emotional state or the like), it may be likely that the user has made experiences associated with the first content. The user content is acquired such that it is associated with the environment information and the first content.

The information processing circuitry provides the second content to the user. The second content is provided to the user according to its content type (as discussed for the first content).

In the above discussed example, the first content may be an image of a previous sports event in a sports arena in a city the vehicle is driving provided as a trigger (cue) to the user and the second content may be determined to be the first content and an image of the user taken at the time the user was visiting a related sports event in the sports arena (selected from the user content).

Accordingly, the second content may have a higher degree of detailedness than the first content or may be a more concrete content or the like, as discussed. Thus, providing the second content to the user may further enhance the impression of the user when recalling past experiences.

The information processing circuitry measures, in response to providing the second content to the user, second user body data of the user and determine, based on the measured second user body data, a second emotional state of the user.

The second user body data may be measured a predetermined time after providing the second content (e.g. 10 seconds or 20 seconds without limiting the disclosure in this regard), which is intended to enhance an emotional reaction, for example, due to refining a recall of a user's past experience.

The second emotional state is determined to the initial and first emotional state of the user. The second emotional state is determined based on the second user body data as discussed for the initial emotional state.

The second emotional state is compared to the initial and first emotional state. In some embodiments, a difference is determined, and the difference is compared, for example, with a threshold in order to determine whether the difference is large enough in order to determine whether the change of the emotional state is large enough. In some embodiments, the difference is further analyzed in order to determine whether the change of the emotional state can be associated with predefined emotional states, e.g. upset, happy, sad, etc.

The information processing circuitry refines, based on a difference between the first emotional state and the second emotional and a difference between the initial emotional state and the second emotional state, the second content provided to the user for increasing the difference between the initial emotional state and the second emotional state of the user.

If the difference between the initial emotional state and the second emotional state and the initial emotional state and the first emotional state is increased (e.g. difference of the values of the user body data is increased (e.g. heart rate, respiration rate, etc.) or the second emotional state is classified as a higher emotional state), it may be likely that the user's impression of the experienced content is enhanced which may be due to an enhanced impression of a past experience of the user by the provided second content.

For further enhancing the user's impression or emotional state, the second content is refined. For example, by adding more details to the provided content (as discussed, the second content may be more detailed, more concrete, or the like).

In the above discussed example, the second content may be the first content (an image of a previous sports event in a sports arena in a city the vehicle is driving) and an image of the user taken at the time the user was visiting a related sports event in the sports arena (selected from the user content). The refined second content includes the previous second content and may further include a sound of fans in the sports arena.

Based on monitoring the emotional state of the user, the second may further be refined by, for example, adding a smell of beer and sausage (which may be artificially generated as discussed above when such aromas are available for release inside the cabin of the vehicle).

Generally, in some embodiments, the refinement process is basically a trial-and-error process in which a hierarchy of content (content pattern) is generated based on a reward given by a change (increase) of the emotional state (emotional response) of the user.

Accordingly, the refined second content may have a higher degree of detailedness than the previous second content or may be a more concrete content or the like, as discussed. Thus, providing the refined second content to the user may further enhance the impression of the user when recalling past experiences.

In some embodiments, if the initial emotional state and the first emotional state of the user are the same or similar (e.g. within a predefined tolerance range or threshold range), the information processing circuitry determines and provides a different first content being associated with the abstract content to the user.

If there is no (or too less) emotional response to the provided first content, the first content may not be related to a personal experience of the user in the past. Thus, different first content (e.g. different images, videos, songs, etc.) may be provided, e.g. in a trial-and-error process, to the user until an emotional response of the user to the provided first content is determined. Once an emotional response is determined, user content associated with the first content and the environment information is acquired and the provided content is refined for increasing the emotional response of the user.

In other words, various types of triggers (cues) as the first content may be presented to the user inside the cabin of the autonomous vehicle based on environment information of the vehicle. These cues may each one of them by themselves or in combination may trigger the recollection of a particular experience of the user in the past. This recollection may be enhanced actively by retrieving content that is representing this particular experience (user content, second content). This content may be presented to the user by means of playing back images/videos, audio, spoken language directly associated with this personal experience and the like. For this, the system searches in a database and matches the content to the experience. Moreover, the experience may be enhanced by the reproduction and release of a smell/odor that was present at the time of the recollected experience. Additionally, a haptic actuator may reproduce the experience of touch.

Basically, this may allow a user to recall a personal experience of the user's past and bringing it back allowing the user to experience it again by closely resembling the sensational experience of the user at the past moment in time. The ability of recollecting past experiences may become a popular feature in future autonomous vehicles due to their nature of providing a self-contained and closed environment allowing undistracted and dedicated entertainment to the user.

The passenger(s) may go virtually back in time when inside the vehicle and may enjoy previous experiences again by exposing the user to an environment/content that closely resembles the reality. Since the vehicle is providing a closed environment, the sensational experience (e.g. smell) may directly targeted to the passenger without dilution. In addition, the user does not need to wear an HMD (head mounted display) or the like which typically may restrict the degree of operating freedom significantly.

In some embodiments, the information processing circuitry obtains user actions from the user. A user action may be an utterance or generally spoken words, an input on (touch) display device or terminal device with a touch display (e.g. smartphone or tablet wirelessly communicating with the circuitry to transmit input data), a gesture recognized with a camera, or the like. Hence, the information processing circuitry may include a microphone to obtain voice data of the user to determine a user action, a touch display device to obtain touch operation to determine a user action, a camera to obtain gesture data of the user to determine a user action.

In some embodiments, the information processing circuitry acquires abstract content data and user content data which is associated with at least one of a date and an obtained first user action of the user.

The abstract content data and the user content data may be associated with the date by acquiring content representing events or experiences that happened, for example, the same day a (or more) year(s) ago.

The first user action may be, for example, an utterance of the user regarding a past experience, e.g., "I remember the last time that I was camping on a place close by some months ago" or the like. Thus, the abstract content may include, e.g., images of a camping place, a fireplace, a sound of rain (it may have rained during the camping) or the like, and the user content may include concrete content of the user regarding that camping trip which is acquired from several databases.

In some embodiments, the information processing circuitry determines the emotional state of the user further based on an obtained second user action.

The second user action may be, for example, an utterance of the user regarding the provided first or second content, e.g., when the first content is an image of an ocean side the user may utter "I like that" or "That looks great" and when the second content is a video from a vacation of the user at the beach the user may utter "That was a great day at the beach". Thus, it is likely that the has an emotional response to the provided content and the emotional state is determined further based on the utterance.

In some embodiments, the information processing circuitry is further configured to trigger acquiring of the abstract content data in response to at least one of random acquisition trigger, a date and an obtained third user action of the user.

The provision of abstract content and its acquisition may be initialized randomly (random acquisition trigger), in response to a date (e.g, always during the week after work of the user for relaxing and enjoying past experiences), in response to a third user action such as an utterance indicating the user may want to recall an experience.

Generally, the information processing circuitry may be configured to implement a machine learning algorithm. In some embodiments, the information processing circuitry is further configured to determine content with a machine learning algorithm. The machine learning algorithm may be a neural network, a decision tree, a support vector machine, etc. or a combination thereof.

The machine learning algorithm may be configured to output a content indication that indicates content that may be provided to the user to optimize the recall of an experience based on the environment data, the previously (already) provided content, the emotional state of the user (user body data) and/or a user action. The machine learning may be continuously trained with environment data, previously provided content, user body data and/or user actions to learn a user response to specific content provided (audio, visual, haptic, smell, etc.) in a specific situation (environment, emotional state, previous provided content, etc.). Hence, the machine learning algorithm learns to optimize content patterns provided to a specific user, which may allow the user to recall an experience more deeply.

Thus, the machine learning may output suggestions for content which may be provided to the user in order to increase recollection of a memory of the user based on learned content patterns for the user and the user response to the content patterns.

Some embodiments pertain to an information processing method for controlling a content provided to a user inside a cabin of an autonomous vehicle, as discussed herein for the information processing circuitry, the method including:
  obtaining environment data;
  acquiring abstract content data, representing abstract content, being associated with the obtained environment data;
  measuring initial user body data of the user and determining, based on the measured initial user body data, an initial emotional state of the user;
  determining and providing a first content, being associated with the abstract content, to the user;
  measuring, in response to providing the first content to the user, first user body data of the user and determining, based on the measured first user body data, a first emotional state of the user; and
  if the initial emotional state and the first emotional state of the user are different:
    acquiring user content data from a database, representing user content associated with a past user experience, being associated with the environment data, wherein the user content is associated with the first content,
    determining, based on a difference between the initial emotional state and the first emotional state of the user, a second content being associated with the user content and being associated with the first content,
    providing the second content to the user,
    measuring, in response to providing the second content to the user, second user body data of the user and determine, based on the measured second user body data, a second emotional state of the user, and
    refining, based on a difference between the first emotional state and the second emotional and a difference between the initial emotional state and the second emotional state, the second content provided to the user for increasing the difference between the initial emotional state and the second emotional state of the user.

The information processing method may be based on or may be implemented or may be carried out by electronic components, integrated circuitry logic, CPU, FPGA, software or in parts by electronic components and in parts by software executed by a processor, the information processing circuitry of the present disclosure, or the like.

The methods as described herein are also implemented in some embodiments as a computer program causing a computer and/or a processor to perform the method, when being carried out on the computer and/or processor. In some embodiments, also a non-transitory computer-readable recording medium is provided that stores therein a computer program product, which, when executed by a processor, such as the processor described above, causes the methods described herein to be performed.

Returning to FIG. 1, which schematically illustrates in a block diagram an embodiment of an autonomous vehicle 1 (in the following: vehicle 1).

The vehicle 1 includes a cabin 2 including a seating area 3 in which a user 4 is present.

The vehicle includes a board-computer 5, a display device 6a, light elements 6b and 6c (6a-c: visual content providing unit), a speaker 7 (audio content providing unit), a smell content providing unit 8, a haptic content providing unit 9 attached to the user 4, a coffee machine 10, an air-conditioner 11, a body sensor unit 12 (not explicitly shown) including body sensors 12a and a brain-machine-interface 12b and a camera 12c, a terminal device 13a and a microphone 13b.. The board-computer 5 is the information processing circuitry of the present disclosure. However, the information processing circuitry may further include the other entities (body sensor unit 12, etc.).

The board-computer 5 has basically two functions which are controlling of the vehicle 1 (the board-computer 5 includes an integrated control unit 7600 which will be discussed below under reference of FIGS. 6 and 7) and implementing the functionality of the information processing circuitry (or information processing system) of the present disclosure. The board-computer 5 is connected to and in communication with all the other devices and sensors (6a-c, 7, 8, 9, 10, 11, 12, 13a-b) in the vehicle 1, e.g., by a bus system, wired and wireless connections, etc. The board-computer 5 communicates over a network 14 (e.g. internet and communication via mobile telecommunications system) with a server 15 of the provider of the vehicle functionality (e.g, a server of the manufacturer), as discussed herein, and with databases DB1-$n$ (e.g. database of a social networking server, a database of a video content provider, a database of a messenger application, a database of a provider of a smart home device, a database of a provider of wearable devices, a database of a music application provider, a database of a financial service provider, a database of an online retail store). The board-computer 5 obtains environment data (representing environment information), e.g., a GPS sensor in the vehicle 1 and imaging sections mounted in/on the vehicle 1 (not shown).

The display device 6a is a television screen, the light elements 6b and 6c are LED tubes each of them provides visual content to the user 4 as part of provided content. The visual content may be images, videos, computer-generated animations, different colors and brightness, and the like.

The speaker 7 provides audio content to the user 4 as part of the provided content. The audio content may be music, verbal communication, sounds, and the like.

The smell content providing unit 8 provides smell content inside the vehicle 1 (cabin of vehicle 1) to the user 4 as part of the provided content. The smell content providing unit 8 includes a plurality of containers including predetermined substances, e.g., gases and liquids having a particular smell such as aromas and the like. One substance or a mixture of substances at a time are released, in accordance with instructions from the board-computer 5, to provide predetermined smells (smell content) to the user 4.

The haptic content providing unit 9 is attached to the user 4 and provides haptic content to the user 4 as part of the provided content. The haptic content providing unit 9 includes a glove including a plurality of small electrodes and the glove is attached to the user's 4 hand. The electrodes provide an electric signal, in accordance with instructions from the board-computer 5, to the skin at the hand of the user, thereby simulating a sense of touch.

The coffee machine 10 produces and provides a coffee (and/or coffee fragrance) to the user 4, in accordance with instructions from the board-computer 5, thereby providing taste content to the user 4.

The air-conditioner 11 heats up or cools down the cabin of the vehicle 1 and controls the humidity inside the cabin of the vehicle 1, in accordance with instructions from the board-computer 5, thereby providing temperature content to the user 4.

The body sensor unit 12 includes the body sensors 12a, the brain-machine-interface 12b, and the camera 12c.

The body sensors 12a include a heart rate sensor, a blood pressure sensor, a body temperature sensor, a respiration rate sensor and a sweat sensor attached to the user 4 that measure a heart rate of the user 4, a blood pressure of the user 4, a body temperature of the user 4, a respiration rate of the user 4 and an amount of sweat of the user 4 as part of user body data.

The brain-machine-interface 12b is a cap attached to the user's 4 head, the cap including a plurality of electric sensors configured to measure electric signals or brain activity of the user 4 in several regions of the brain of the user 4 as part of the user body data, for example, a region associated with a memory of the user 4.

The camera 12c takes images of the user 4 based on which gestures and mimics of the user 4 are determined as part of the user body data.

The measured values or signals or images of the body sensors 12a, the brain-machine-interface 12b and the camera 12c are the user body data and are transmitted to the board-computer 5 for determining an emotional state of the user.

The terminal device 13a and the microphone 13b are a user input unit which obtain user input(s) based on which a user action is obtained (or determined). The user action may be an utterance of the user 4 recorded by the microphone 13b or a touch operation of the user 4 on the terminal device 13a.

Figure 2:
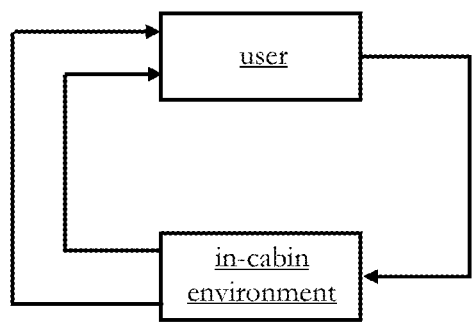
FIG. 2 schematically illustrates in a block diagram a control principle of a content provided to a user inside a cabin of an autonomous vehicle.

FIG. 2 schematically illustrates in a block diagram a control principle of a content provided to a user inside a cabin of an autonomous vehicle such as the autonomous vehicle 1 of the embodiment according to FIG. 1.

The user 4 in the vehicle 1 in-cabin environment is provided with various sorts of content which address the visual sense, the sense of hearing, the sense of smell, the sense of touch, etc. An emotional response to the provided content may be triggered due to a past user experience which is associated with the provided content. The provided content is varied in time and type and the degree of detailedness is increased if the provided content triggers an emotional response which basically represents a reward system (or reinforcement system) until a content pattern is found which has increased the emotional response to the provided content to the user 4. This may allow the user 4 to recall past experiences with an enhanced sense of reality.

In other words, an emotion recognition system assesses captured signals of the different sensing modalities (body sensors etc.). This emotion recognition system identifies which cue (trigger, content) has the strongest impact in the recall of the user's memories/experiences. The system then emphasizes actuators (content providing units) that trigger this emotional response to build a reinforcement system. In this way, the system is personalized to the individual user 4 making sure that those cues are utilized the most which lead to a strong recall of memories/experiences from the past.

Figure 3:
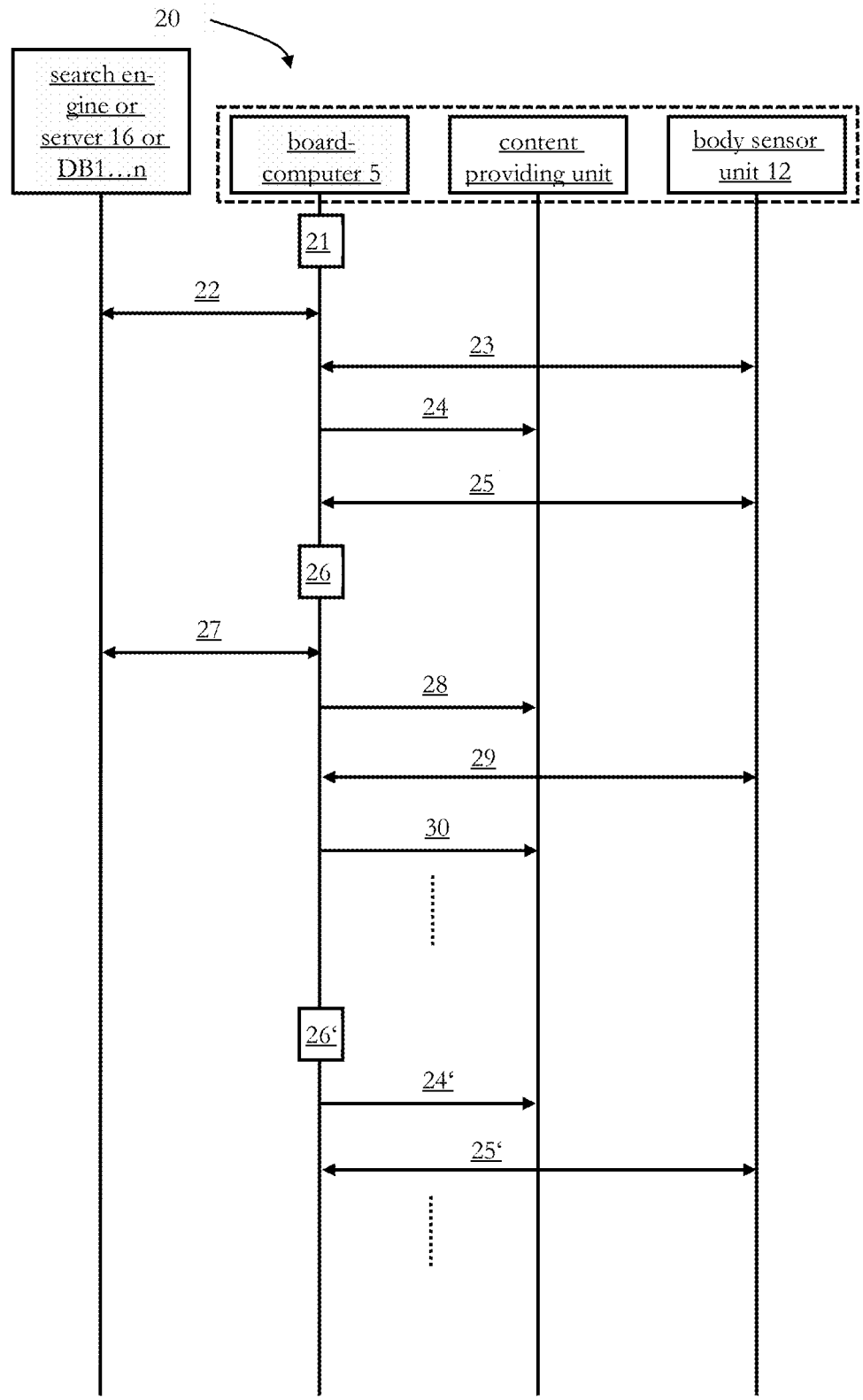
FIG. 3 schematically illustrates in a state diagram a first embodiment of an information processing method for an exemplarily scenario.

FIG. 3 schematically illustrates in a state diagram a first embodiment of an information processing method 20 for an exemplarily scenario.

The server 15, the databases DB1-$n$, the board-computer 5 and the body sensor unit 12 correspond to the respective entities of the embodiment according to FIG. 1. The search engine may be an arbitrary search engine in the internet, as discussed herein. The content providing unit 16 corresponds to the display device 6a, the light elements 6b and 6c, the speaker 7, the smell content providing unit 8 and the haptic content providing unit 9 of the embodiment according to FIG. 1. The board-computer 5 is the information processing circuitry of the present disclosure. However, the information processing circuitry may further include the body sensor unit 12 and the content providing unit 16.

In the following it is assumed that the vehicle 1 is driving on a street close to an ocean side.

Then, at 21, the board-computer 5 obtains environment data representing environment information. The environment data includes location data of the vehicle 1 representing a location of the vehicle 1 and map data from a detailed digital map, wherein the map data represents information about places, a landscape and the like in a predetermined distance (e.g. 5 km) around the location of the vehicle 1. The location of the vehicle 1 and the landscape information indicate that an ocean side is close.

Then, at 22, the board-computer 5 acquires abstract content data, representing abstract content, which is associated with the obtained environment data. The board-computer 5 transmits a search command including the location and the landscape information via the network 14 to query the search engine and the server 15 for the abstract content associated with the obtained environment information. The search engine and the server 15 send back the abstract content to the board-computer 5 which stores the abstract content.

Here, the abstract content may be an image of the ocean side, a sound of ocean waves at the beach of the ocean side and predetermined smell data representing a smell content indicative for a smell of the ocean side (the smell data indicate how the plurality of predetermined substances in the smell content providing unit 8 have to be released in order to simulate such ocean smell).

Then, at 23, the board-computer instructs the body sensor unit 12 to measure initial user body data of the user 4. The body sensor unit 12 transmits the user body data to the board-computer 5. The board-computer 5 determines, based on the measured initial user body data, an initial emotional state of the user 4, as discussed herein. The initial emotional state of the user 4 is taken as a reference to determine whether the emotional state of the user 4 has changed in response to providing content to the user 4.

Then, at 24, the board-computer 5 determines a first content which is associated with the abstract content and provides the first content to the user 4. Here, the first content may be the image of the ocean side and computer-generated animations of sailing boats in the ocean which are laid over the image. The first content is provided via the display device 6a to the user.

Then, at 25, the board-computer 5 instructs the body sensor unit 12 to measure, in response to providing the first content to the user 4, first user body data of the user 4. The body sensor unit 12 transmits the first user body data to the board-computer 5. The board-computer 5 determines, based on the measured first user body data, a first emotional state of the user 4, as discussed herein.

Then, at 26, the board-computer 5 determines that the initial emotional state of the user 4 and the first emotional state of the user 4 are different. Thus, it may be likely that the user 4 has made a past experience associated with the provided first content and the environment information.

Then, at 27, the board-computer 5 acquires user content data from the databases DB1-*n*, representing user content associated with a past user experience, which is associated with the environment data representing environment information and the first content. The board-computer 5 transmits a search command including the location, the landscape information, information about the image of the ocean and the animated sailing boats via the network 14 to query the databases DB1-*n*. for the user content. The databases DB1-*n* send back the user content to the board-computer 5 which stores the user content.

Here, the user content may be a video of the user 4 and a partner or friend or family member of the user 4 that was recorded during a vacation of the user 4 at an ocean side and a song the user 4 used to listen to during the vacation at the ocean side.

Then, at 28, the board-computer 5 determines, based on a difference between the initial emotional state and the first emotional state of the user, a second content which is associated with the user content and with the first content.

If there is an emotional response (difference between the initial emotional state and the first emotional state) to the first content (image of the ocean side with animations, visual content), but this response is small (based on the difference between the initial emotional state and the first emotional state), the second content may be of a different type such as audio content.

Here, the second content may thus be the song the user 4 used to listen to during the vacation at the ocean side (in addition to the first content) which may likely increase the emotional response of the user 4. The second content is provided to the user via the speaker 7 in the vehicle 1. This may enhance the recall of the past experience of the user 4.

Then, at 29, the board-computer 5 instructs the body sensor unit 12 to measure, in response to providing the first content to the user 4, second user body data of the user 4. The body sensor unit 12 transmits the second user body data to the board-computer 5. The board-computer 5 determines, based on the measured second user body data, a second emotional state of the user 4, as discussed herein.

Then, at 30, a refinement process starts. The board-computer 5 refines, based on a difference between the first emotional state and the second emotional and a difference between the initial emotional state and the second emotional state, the second content provided to the user 4 for increasing the difference between the initial emotional state and the second emotional state of the user 4.

The refined second content may include additionally the video of the user 4 during the vacation at the ocean side. The refined second content may include further content from the abstract content, for example, the sound of ocean waves at the beach of the ocean side and the predetermined smell data representing a smell content indicative for a smell of the ocean side.

Moreover, the refined second content may include touch content, for example, if the partner of the user 4 has touched the arm of the user 4 in the video.

Additionally, the light elements 6b and 6c may instructed to turn down the light if the video was taken during sunset, for example.

Accordingly, the refinement process is basically a trial-and-error process in which a hierarchy of content (content pattern) is generated based on a reward given by a change (increase) of the emotional state (emotional response) of the user.

Accordingly, the refined second content may have a higher degree of detailedness than the previous second content and providing the refined second content to the user may further enhance the impression of the user when recalling past experiences.

At 26', in contrast to 26, the board-computer 5 determines that the initial emotional state and the first emotional state of the user are the same.

Then, at 24', the board-computer 5 determines and provides a different first content which is associated with the abstract content. The different first content may be the sound of ocean waves at the beach of the ocean side and the predetermined smell data representing a smell content indicative for a smell of the ocean side.

Then, at 25', the board-computer 5 instructs the body sensor unit 12 to measure, in response to providing the different first content to the user 4, first user body data of the user 4. The body sensor unit 12 transmits the first user body data to the board-computer 5. The board-computer 5 determines, based on the measured first user body data, a first emotional state of the user 4, as discussed herein. A difference to the initial emotional state is determined and the process either goes back to 26' or moves on with 27 and following.

Accordingly, the first content is provided in a trial-and-error process to the user until an emotional response of the user to the provided first content is determined.

Figure 4:
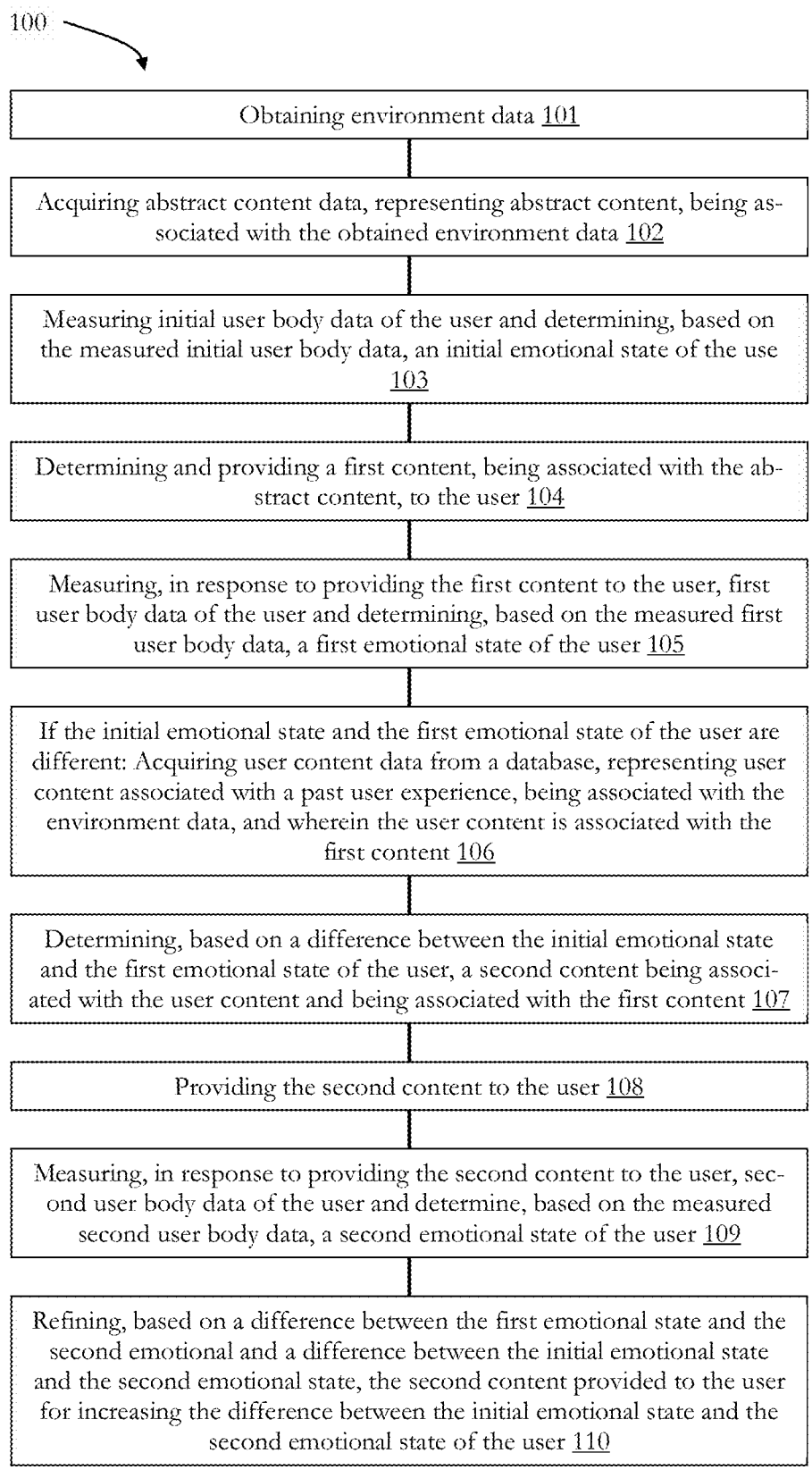
FIG. 4 schematically illustrates in a flow diagram a second embodiment of an information processing method.

FIG. 4 schematically illustrates in a flow diagram a second embodiment of an information processing method 100 (which is carried out by an information processing circuitry according to the present disclosure).

At 101, environment data is obtained, as discussed herein.

At 102, abstract content data is acquired, representing abstract content which is associated with the obtained environment data, as discussed herein.

At 103, initial user body data of the user is measured and, based on the measured initial user body data, an initial emotional state of the user is determined, as discussed herein.

At 104, a first content, which is associated with the abstract content, is determined and provided to the user, as discussed herein.

At 105, first user body data of the user is measured in response to providing the first content to the user and, based on the measured first user body data, a first emotional state of the user is determined, as discussed herein.

At 106, if the initial emotional state and the first emotional state of the user are different, user content data is acquired from a database, representing user content associated with a past user experience, which is associated with the environment data, and wherein the user content is associated with the first content, as discussed herein.

At 107, based on a difference between the initial emotional state and the first emotional state of the user, a second content which is associated with the user content and being associated with the first content is determined, as discussed herein.

At 108, the second content is provided to the user, as discussed herein.

At 109, in response to providing the second content to the user, second user body data of the user is measured and, based on the measured second user body data, a second emotional state of the user is determined, as discussed herein.

At 110, based on a difference between the first emotional state and the second emotional and a difference between the initial emotional state and the second emotional state, the second content provided to the user is refined for increasing the difference between the initial emotional state and the second emotional state of the user, as discussed herein.

Figure 5:
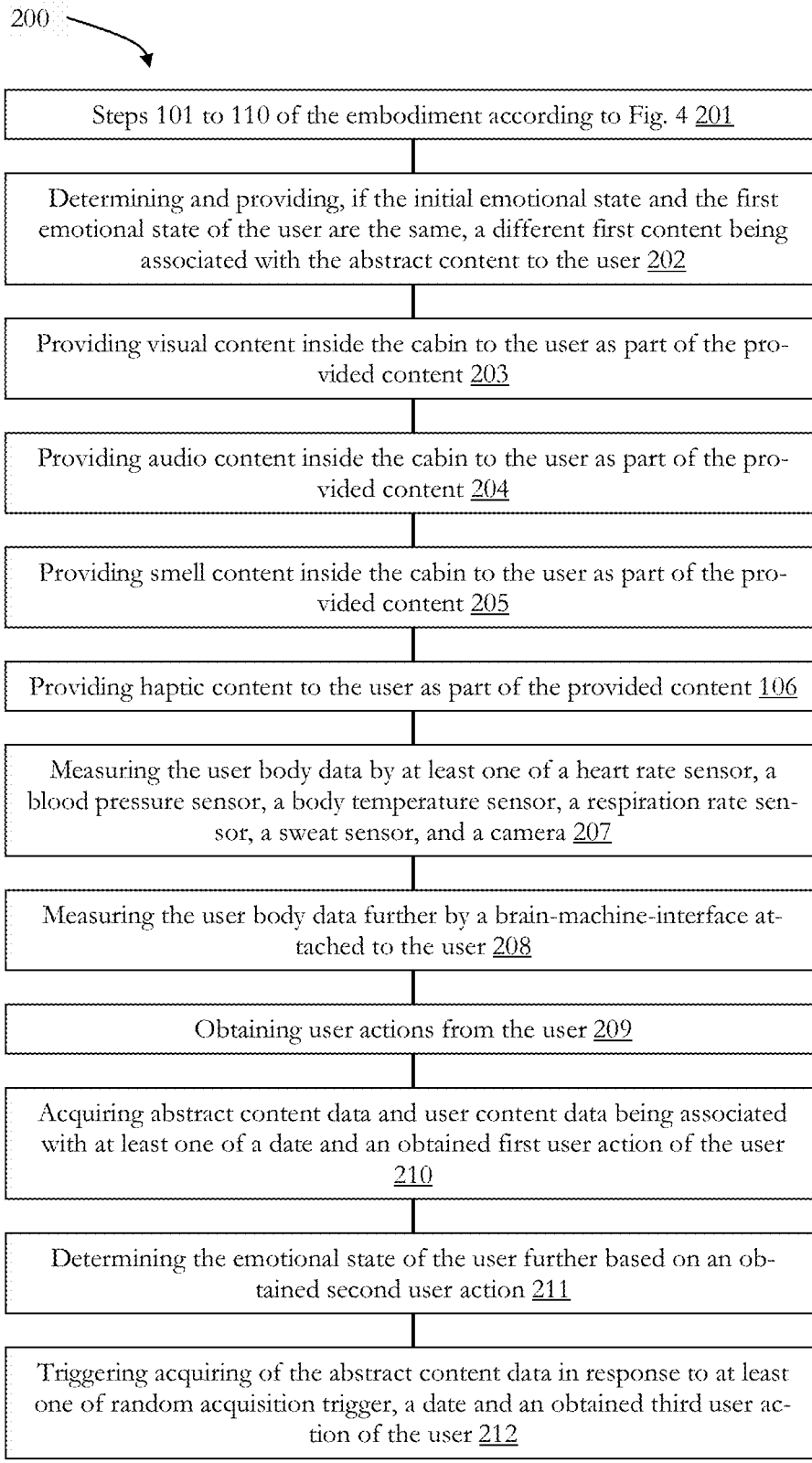
FIG. 5 schematically illustrated in a flow diagram a third embodiment of an information processing method.

FIG. 5 schematically illustrates in a flow diagram a third embodiment of an information processing method 200 (which is carried out by an information processing circuitry according to the present disclosure).

At 201, the steps 101 to 110 of the embodiment according to FIG. 4 are carried out, which is referred to and incorporated by reference here to avoid unnecessary repetitions.

At 202, if the initial emotional state and the first emotional state of the user are the same, a different first content which is associated with the abstract content is determined and provided to the user, as discussed herein.

At 203, visual content is provided inside the cabin to the user as part of the provided content, as discussed herein.

At 204, audio content is provided inside the cabin to the user as part of the provided content, as discussed herein.

At 205, smell content is provided inside the cabin to the user as part of the provided content, as discussed herein.

At 206, haptic content is provided to the user as part of the provided content, as discussed herein.

At 207, the user body data is measured by at least one of a heart rate sensor, a blood pressure sensor, a body temperature sensor, a respiration rate sensor, a sweat sensor, and a camera, as discussed herein.

At 208, the user body data is further measured by a brain-machine-interface attached to the user, as discussed herein.

At 209, user actions are obtained from the user, as discussed herein.

At 210, abstract content data and user content data which associated with at least one of a date and an obtained first user action of the user is acquired, as discussed herein.

At 211, the emotional state of the user is determined further based on an obtained second user action, as discussed herein.

At 212, acquiring of the abstract content data is triggered in response to at least one of random acquisition trigger, a date and an obtained third user action of the user, as discussed herein.

Figure 6:
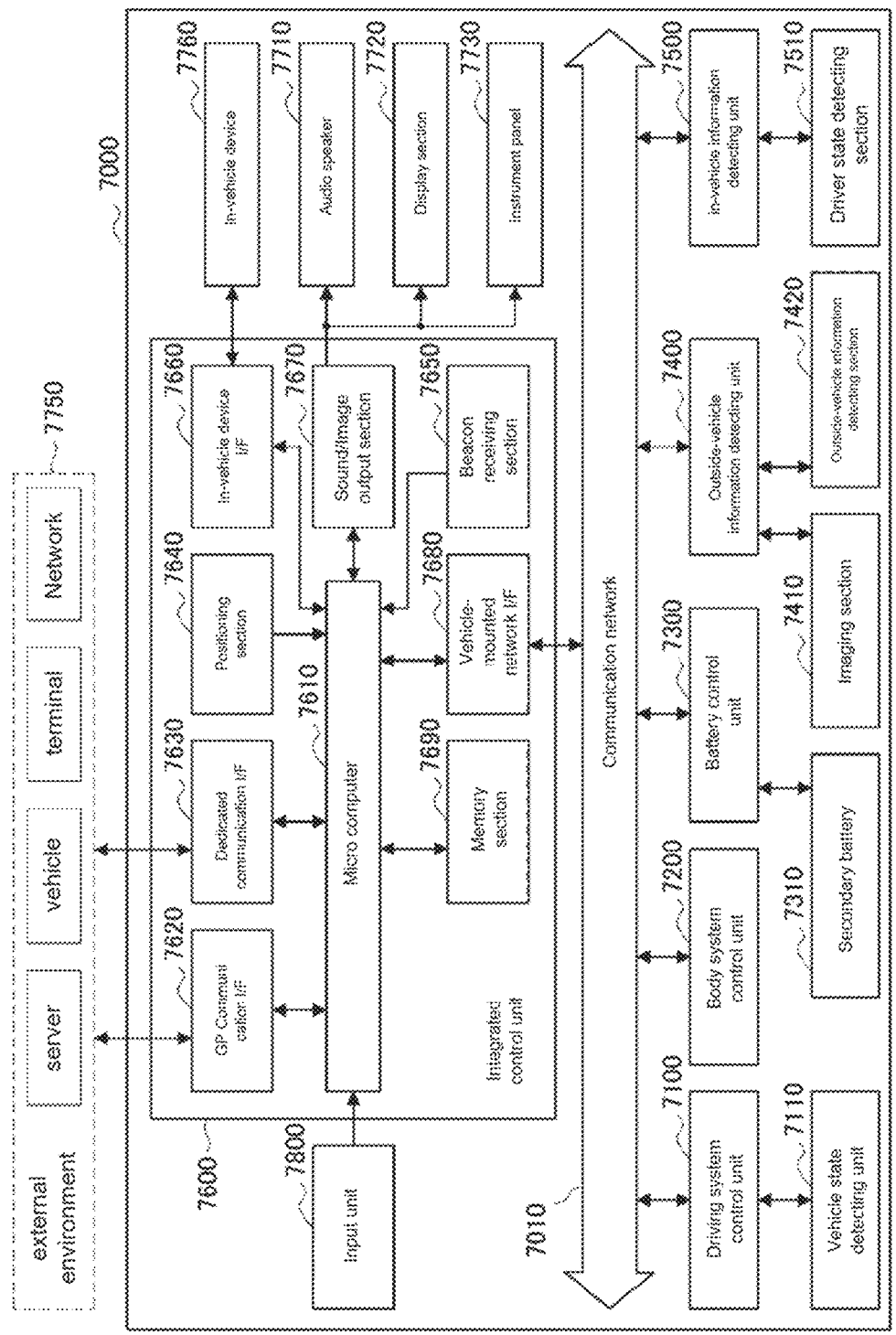
FIG. 6 schematically illustrates in a block diagram an embodiment of a schematic configuration of a vehicle control system.

FIG. 6 schematically illustrates in a block diagram an embodiment of a schematic configuration of a vehicle control system 7000 for an autonomous vehicle such as the autonomous vehicle 1 of the embodiment according to FIG. 1.

The vehicle control system 7000 includes a plurality of electronic control units connected to each other via a communication network 7010. In the example depicted in FIG. 6, the vehicle control system 7000 includes a driving system control unit 7100, a body system control unit 7200, a battery control unit 7300, an outside-vehicle information detecting unit 7400, an in-vehicle information detecting unit 7500, and an integrated control unit 7600. The communication network 7010 connecting the plurality of control units to each other may, for example, be a vehicle-mounted communication network compliant with an arbitrary standard such as controller area network (CAN), local interconnect network (LIN), local area network (LAN), FlexRay (registered trademark), or the like.

Each of the control units includes: a microcomputer that performs arithmetic processing according to various kinds of programs; a storage section that stores the programs executed by the microcomputer, parameters used for various kinds of operations, or the like; and a driving circuit that drives various kinds of control target devices. Each of the control units further includes: a network interface (I/F) for performing communication with other control units via the communication network 7010; and a communication I/F for performing communication with a device, a sensor, or the like within and without the vehicle by wire communication or radio communication. A functional configuration of the integrated control unit 7600 illustrated in FIG. 6 includes a microcomputer 7610, a general-purpose communication I/F 7620, a dedicated communication I/F 7630, a positioning section 7640, a beacon receiving section 7650, an in-vehicle device I/F 7660, a sound/image output section 7670, a vehicle-mounted network I/F 7680, and a storage section 7690. The other control units similarly include a microcomputer, a communication I/F, a storage section, and the like.

The board-computer 5 of the embodiment discussed under reference of FIG. 1 includes the integrated control unit 7600 for vehicle control.

The microcomputer 7610 of the integrated control unit 7600 is used for executing the information processing method in accordance with the present disclosure.

The environment data is obtained, e.g., from the outside-vehicle information detecting unit 7400 (which will be discussed further below) and the in-vehicle information detecting unit 7500 (which will be discussed further below).

The general-purpose communication I/F 7620 is used to communicate with the network and to query the databases, the server and the search engine in order to acquire the abstract content and the user content. The storage section 7690 may store the acquired abstract content and the user content.

An audio speaker 7710 (which will be discussed further below) corresponds to the speaker 7 of the embodiment discussed under reference of FIG. 1. A display section 7720 (which will be discussed further below) corresponds to the display device 6*a* of the embodiment discussed under reference of FIG. 1. The audio speaker 7710 and the display section 7720 provide cues and content to the user which a visual and audio content type.

An in-vehicle device 7760 (which will be discussed further below) may correspond to the terminal device 13*a* of the embodiment discussed under reference of FIG. 1.

Although not shown in FIG. 6, the vehicle control system 7000 may further include the light elements 6*b* and 6*c*, the smell content providing unit 8, the haptic content providing unit 9, the coffee machine 10, the air-conditioner 11, the body sensor unit 12 and the microphone 13*b* of the embodiment discussed under reference of FIG. 1. The integrated control unit 7600 may further control these entities and execute the information processing method in accordance with the present disclosure.

The driving system control unit 7100 controls the operation of devices related to the driving system of the vehicle in accordance with various kinds of programs. For example, the driving system control unit 7100 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like. The driving system control unit 7100 may have a function as a control device of an antilock brake system (ABS), electronic stability control (ESC), or the like.

The driving system control unit 7100 is connected with a vehicle state detecting section 7110. The vehicle state detecting section 7110, for example, includes at least one of a gyro sensor that detects the angular velocity of axial rotational movement of a vehicle body, an acceleration sensor that detects the acceleration of the vehicle, and sensors for detecting an amount of operation of an accelerator pedal, an amount of operation of a brake pedal, the steering angle of a steering wheel, an engine speed or the rotational speed of wheels, and the like. The driving system control unit 7100 performs arithmetic processing using a signal input from the vehicle state detecting section 7110, and controls the internal combustion engine, the driving motor, an electric power steering device, the brake device, and the like.

The body system control unit 7200 controls the operation of various kinds of devices provided to the vehicle body in accordance with various kinds of programs. For example, the body system control unit 7200 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 7200. The body system control unit 7200 receives these input radio waves or signals, and controls a door lock device, the power window device, the lamps, or the like of the vehicle.

The battery control unit 7300 controls a secondary battery 7310, which is a power supply source for the driving motor, in accordance with various kinds of programs. For example, the battery control unit 7300 is supplied with information about a battery temperature, a battery output voltage, an amount of charge remaining in the battery, or the like from a battery device including the secondary battery 7310. The battery control unit 7300 performs arithmetic processing using these signals, and performs control for regulating the temperature of the secondary battery 7310 or controls a cooling device provided to the battery device or the like.

The outside-vehicle information detecting unit 7400 detects information about the outside of the vehicle including the vehicle control system 7000. For example, the outside-vehicle information detecting unit 7400 is connected with at least one of an imaging section 7410 and an outside-vehicle information detecting section 7420. The imaging section 7410 includes at least one of a time-of-flight (ToF) camera, a stereo camera, a monocular camera, an infrared camera, and other cameras. The outside-vehicle information detecting section 7420, for example, includes at least one of an environmental sensor for detecting current atmospheric conditions or weather conditions and a peripheral information detecting sensor for detecting another vehicle, an obstacle, a pedestrian, or the like on the periphery of the vehicle including the vehicle control system 7000.

The environmental sensor, for example, may be at least one of a rain drop sensor detecting rain, a fog sensor detecting a fog, a sunshine sensor detecting a degree of sunshine, and a snow sensor detecting a snowfall. The peripheral information detecting sensor may be at least one of an ultrasonic sensor, a radar device, and a LIDAR device (Light detection and Ranging device, or Laser imaging detection and ranging device). Each of the imaging section 7410 and the outside-vehicle information detecting section 7420 may be provided as an independent sensor or device, or may be provided as a device in which a plurality of sensors or devices are integrated.

Figure 7:
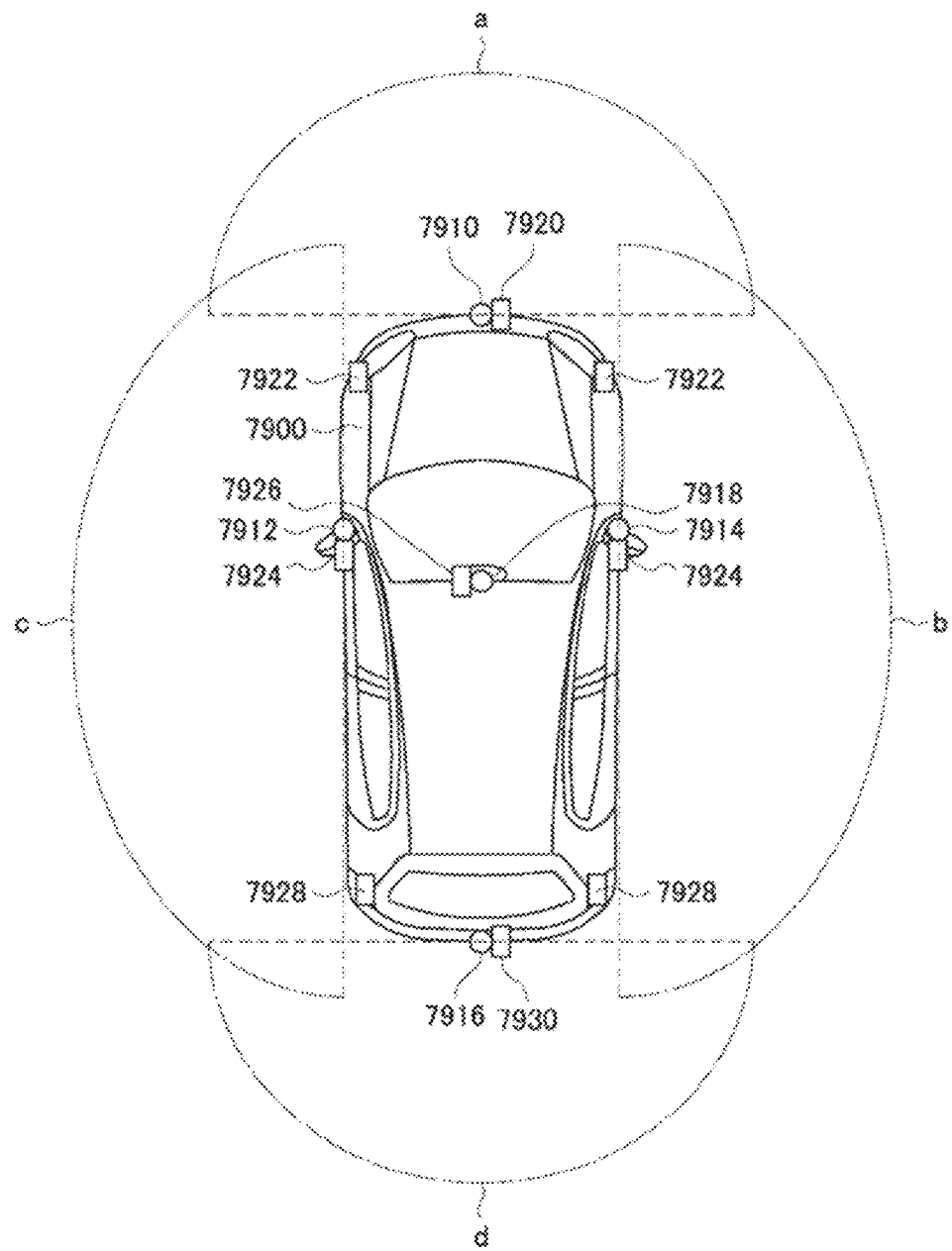
FIG. 7 schematically illustrates a diagram of assistance in explaining an embodiment of installation positions of an outside-vehicle information detecting section and an imaging section.

FIG. 7 schematically illustrates a diagram of assistance in explaining an embodiment of installation positions of the outside-vehicle information detecting section 7420 and the imaging section 7410.

Imaging sections 7910, 7912, 7914, 7916, and 7918 are, for example, disposed at at least one of positions on a front nose, sideview mirrors, a rear bumper, and a back door of the vehicle 7900 and a position on an upper portion of a windshield within the interior of the vehicle. The imaging section 7910 provided to the front nose and the imaging section 7918 provided to the upper portion of the windshield within the interior of the vehicle obtain mainly an image of the front of the vehicle 7900. The imaging sections 7912 and 7914 provided to the sideview mirrors obtain mainly an image of the sides of the vehicle 7900. The imaging section 7916 provided to the rear bumper or the back door obtains mainly an image of the rear of the vehicle 7900. The imaging section 7918 provided to the upper portion of the windshield within the interior of the vehicle is used mainly to detect a preceding vehicle, a pedestrian, an obstacle, a signal, a traffic sign, a lane, or the like.

Incidentally, FIG. 7 depicts an example of photographing ranges of the respective imaging sections 7910, 7912, 7914, and 7916. An imaging range a represents the imaging range of the imaging section 7910 provided to the front nose. Imaging ranges b and c respectively represent the imaging ranges of the imaging sections 7912 and 7914 provided to the sideview mirrors. An imaging range d represents the imaging range of the imaging section 7916 provided to the rear bumper or the back door. A bird's-eye image of the vehicle 7900 as viewed from above can be obtained by superimposing image data imaged by the imaging sections 7910, 7912, 7914, and 7916, for example.

Outside-vehicle information detecting sections 7920, 7922, 7924, 7926, 7928, and 7930 provided to the front, rear, sides, and corners of the vehicle 7900 and the upper portion of the windshield within the interior of the vehicle may be, for example, an ultrasonic sensor or a radar device. The outside-vehicle information detecting sections 7920, 7926, and 7930 provided to the front nose of the vehicle 7900, the rear bumper, the back door of the vehicle 7900, and the upper portion of the windshield within the interior of the vehicle may be a LIDAR device, for example. These outside-vehicle information detecting sections 7920 to 7930 are used mainly to detect a preceding vehicle, a pedestrian, an obstacle, or the like.

Returning to FIG. 6, the description will be continued. The outside-vehicle information detecting unit 7400 makes the imaging section 7410 image an image of the outside of the vehicle, and receives imaged image data. In addition, the outside-vehicle information detecting unit 7400 receives detection information from the outside-vehicle information detecting section 7420 connected to the outside-vehicle information detecting unit 7400. In a case where the outside-vehicle information detecting section 7420 is an ultrasonic sensor, a radar device, or a LIDAR device, the outside-vehicle information detecting unit 7400 transmits an ultrasonic wave, an electromagnetic wave, or the like, and receives information of a received reflected wave. On the basis of the received information, the outside-vehicle information detecting unit 7400 may perform processing of detecting an object such as a human, a vehicle, an obstacle, a sign, a character on a road surface, or the like, or processing of detecting a distance thereto. The outside-vehicle information detecting unit 7400 may perform environment recognition processing of recognizing a rainfall, a fog, road surface conditions, or the like on the basis of the received information. The outside-vehicle information detecting unit 7400 may calculate a distance to an object outside the vehicle on the basis of the received information.

In addition, on the basis of the received image data, the outside-vehicle information detecting unit 7400 may perform image recognition processing of recognizing a human, a vehicle, an obstacle, a sign, a character on a road surface, or the like, or processing of detecting a distance thereto. The outside-vehicle information detecting unit 7400 may subject the received image data to processing such as distortion correction, alignment, or the like, and combine the image data imaged by a plurality of different imaging sections 7410 to generate a bird's-eye image or a panoramic image. The outside-vehicle information detecting unit 7400 may perform viewpoint conversion processing using the image data imaged by the imaging section 7410 including the different imaging parts.

The in-vehicle information detecting unit 7500 detects information about the inside of the vehicle. The in-vehicle information detecting unit 7500 is, for example, connected with a driver state detecting section 7510 that detects the state of a driver. The driver state detecting section 7510 may include a camera that images the driver, a biosensor that detects biological information of the driver, a microphone that collects sound within the interior of the vehicle, or the like. The bio sensor is, for example, disposed in a seat surface, the steering wheel, or the like, and detects biological information of an occupant sitting in a seat or the driver holding the steering wheel. On the basis of detection information input from the driver state detecting section 7510, the in-vehicle information detecting unit 7500 may calculate a degree of fatigue of the driver or a degree of concentration of the driver, or may determine whether the driver is dozing. The in-vehicle information detecting unit 7500 may subject an audio signal obtained by the collection of the sound to processing such as noise canceling processing or the like.

The integrated control unit 7600 controls general operation within the vehicle control system 7000 in accordance with various kinds of programs. The integrated control unit 7600 is connected with an input section 7800. The input section 7800 is implemented by a device capable of input operation by an occupant, such, for example, as a touch panel, a button, a microphone, a switch, a lever, or the like. The integrated control unit 7600 may be supplied with data obtained by voice recognition of voice input through the microphone. The input section 7800 may, for example, be a remote control device using infrared rays or other radio waves, or an external connecting device such as a mobile telephone, a personal digital assistant (PDA), or the like that supports operation of the vehicle control system 7000. The input section 7800 may be, for example, a camera. In that case, an occupant can input information by gesture. Alternatively, data may be input which is obtained by detecting the movement of a wearable device that an occupant wears. Further, the input section 7800 may, for example, include an input control circuit or the like that generates an input signal on the basis of information input by an occupant or the like using the above-described input section 7800, and which outputs the generated input signal to the integrated control unit 7600. An occupant or the like inputs various kinds of data or gives an instruction for processing operation to the vehicle control system 7000 by operating the input section 7800.

The storage section 7690 may include a read only memory (ROM) that stores various kinds of programs executed by the microcomputer and a random access memory (RAM) that stores various kinds of parameters, operation results, sensor values, or the like. In addition, the storage section 7690 may be implemented by a magnetic storage device such as a hard disc drive (HDD) or the like, a semiconductor storage device, an optical storage device, a magneto-optical storage device, or the like.

The general-purpose communication I/F 7620 is a communication I/F used widely, which communication I/F mediates communication with various apparatuses present in an external environment 7750. The general-purpose communication I/F 7620 may implement a cellular communication protocol such as global system for mobile communications (GSM (registered trademark)), worldwide interoperability for microwave access (WiMAX (registered trademark)), long term evolution (LTE (registered trademark)), LTE-advanced (LTE-A), or the like, or another wireless communication protocol such as wireless LAN (referred to also as wireless fidelity (Wi-Fi (registered trademark)), Bluetooth (registered trademark), or the like. The general-purpose communication I/F 7620 may, for example, connect to an apparatus (for example, an application server or a control server) present on an external network (for example, the Internet, a cloud network, or a company-specific network) via a base station or an access point. In addition, the general-purpose communication I/F 7620 may connect to a terminal present in the vicinity of the vehicle (which terminal is, for example, a terminal of the driver, a pedestrian, or a store, or a machine type communication (MTC) terminal) using a peer to peer (P2P) technology, for example.

The dedicated communication I/F 7630 is a communication I/F that supports a communication protocol developed for use in vehicles. The dedicated communication I/F 7630 may implement a standard protocol such, for example, as wireless access in vehicle environment (WAVE), which is a combination of institute of electrical and electronic engineers (IEEE) 802.11p as a lower layer and IEEE 1609 as a higher layer, dedicated short range communications (DSRC), or a cellular communication protocol. The dedicated communication I/F 7630 typically carries out V2X communication as a concept including one or more of communication between a vehicle and a vehicle (Vehicle to Vehicle), communication between a road and a vehicle (Vehicle to Infrastructure), communication between a vehicle and a home (Vehicle to Home), and communication between a pedestrian and a vehicle (Vehicle to Pedestrian).

The positioning section 7640, for example, performs positioning by receiving a global navigation satellite system (GNSS) signal from a GNSS satellite (for example, a GPS signal from a global positioning system (GPS) satellite), and generates positional information including the latitude, longitude, and altitude of the vehicle. Incidentally, the positioning section 7640 may identify a current position by exchanging signals with a wireless access point, or may obtain the positional information from a terminal such as a mobile telephone, a personal handyphone system (PHS), or a smart phone that has a positioning function.

The beacon receiving section 7650, for example, receives a radio wave or an electromagnetic wave transmitted from a radio station installed on a road or the like, and thereby obtains information about the current position, congestion, a closed road, a necessary time, or the like. Incidentally, the function of the beacon receiving section 7650 may be included in the dedicated communication I/F 7630 described above.

The in-vehicle device I/F 7660 is a communication interface that mediates connection between the microcomputer 7610 and various in-vehicle devices 7760 present within the vehicle. The in-vehicle device I/F 7660 may establish wireless connection using a wireless communication protocol such as wireless LAN, Bluetooth (registered trademark), near field communication (NFC), or wireless universal serial bus (WUSB). In addition, the in-vehicle device I/F 7660 may establish wired connection by universal serial bus (USB), high-definition multimedia interface (HDMI (registered trademark)), mobile high-definition link (MHL), or the like via a connection terminal (and a cable if necessary) not depicted in the figures. The in-vehicle devices 7760 may, for example, include at least one of a mobile device and a wearable device possessed by an occupant and an information device carried into or attached to the vehicle. The in-vehicle devices 7760 may also include a navigation device that searches for a path to an arbitrary destination. The in-vehicle device I/F 7660 exchanges control signals or data signals with these in-vehicle devices 7760.

The vehicle-mounted network I/F 7680 is an interface that mediates communication between the microcomputer 7610 and the communication network 7010. The vehicle-mounted network I/F 7680 transmits and receives signals or the like in conformity with a predetermined protocol supported by the communication network 7010.

The microcomputer 7610 of the integrated control unit 7600 controls the vehicle control system 7000 in accordance with various kinds of programs on the basis of information obtained via at least one of the general-purpose communication I/F 7620, the dedicated communication I/F 7630, the positioning section 7640, the beacon receiving section 7650, the in-vehicle device I/F 7660, and the vehicle-mounted network I/F 7680. For example, the microcomputer 7610 may calculate a control target value for the driving force generating device, the steering mechanism, or the braking device on the basis of the obtained information about the inside and outside of the vehicle, and output a control command to the driving system control unit 7100. For example, the microcomputer 7610 may perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like. In addition, the microcomputer 7610 may perform cooperative control intended for automatic driving, which makes the vehicle to travel autonomously without depending on the operation of the driver, or the like, by controlling the driving force generating device, the steering mechanism, the braking device, or the like on the basis of the obtained information about the surroundings of the vehicle.

The microcomputer 7610 may generate three-dimensional distance information between the vehicle and an object such as a surrounding structure, a person, or the like, and generate local map information including information about the surroundings of the current position of the vehicle, on the basis of information obtained via at least one of the general-purpose communication I/F 7620, the dedicated communication I/F 7630, the positioning section 7640, the beacon receiving section 7650, the in-vehicle device I/F 7660, and the vehicle-mounted network I/F 7680. In addition, the micro-computer 7610 may predict danger such as collision of the vehicle, approaching of a pedestrian or the like, an entry to a closed road, or the like on the basis of the obtained information, and generate a warning signal. The warning signal may, for example, be a signal for producing a warning sound or lighting a warning lamp.

The sound/image output section 7670 transmits an output signal of at least one of a sound and an image to an output device capable of visually or auditorily notifying information to an occupant of the vehicle or the outside of the vehicle. In the example of FIG. 6, an audio speaker 7710, a display section 7720, and an instrument panel 7730 are illustrated as the output device. The display section 7720 may, for example, include at least one of an on-board display and a head-up display. The display section 7720 may have an augmented reality (AR) display function. The output device may be other than these devices, and may be another device such as headphones, a wearable device such as an eyeglass type display worn by an occupant or the like, a projector, a lamp, or the like. In a case where the output device is a display device, the display device visually displays results obtained by various kinds of processing performed by the microcomputer 7610 or information received from another control unit in various forms such as text, an image, a table, a graph, or the like. In addition, in a case where the output device is an audio output device, the audio output device converts an audio signal constituted of reproduced audio data or sound data or the like into an analog signal, and auditorily outputs the analog signal.

Incidentally, at least two control units connected to each other via the communication network 7010 in the example depicted in FIG. 6 may be integrated into one control unit. Alternatively, each individual control unit may include a plurality of control units. Further, the vehicle control system 7000 may include another control unit not depicted in the figures. In addition, part or the whole of the functions performed by one of the control units in the above description may be assigned to another control unit. That is, predetermined arithmetic processing may be performed by any of the control units as long as information is transmitted and received via the communication network 7010. Similarly, a sensor or a device connected to one of the control units may be connected to another control unit, and a plurality of control units may mutually transmit and receive detection information via the communication network 7010.

It should be recognized that the embodiments describe methods with an exemplary ordering of method steps. The specific ordering of method steps is however given for illustrative purposes only and should not be construed as binding.

All units and entities described in this specification and claimed in the appended claims can, if not stated otherwise, be implemented as integrated circuit logic, for example on a chip, and functionality provided by such units and entities can, if not stated otherwise, be implemented by software.

In so far as the embodiments of the disclosure described above are implemented, at least in part, using software-controlled data processing apparatus, it will be appreciated that a computer program providing such software control and a transmission, storage or other medium by which such a computer program is provided are envisaged as aspects of the present disclosure.

Note that the present technology can also be configured as described below.

(1) An information processing circuitry for controlling a content provided to a user inside a cabin of an autonomous vehicle, wherein the information processing circuitry is configured to:
  obtain environment data;
  acquire abstract content data, representing abstract content, being associated with the obtained environment data;
  measure initial user body data of the user and determine, based on the measured initial user body data, an initial emotional state of the user;
  determine and provide a first content, being associated with the abstract content, to the user;
  measure, in response to providing the first content to the user, first user body data of the user and determine, based on the measured first user body data, a first emotional state of the user; and
  if the initial emotional state and the first emotional state of the user are different:
    acquire user content data from a database, representing user content associated with a past user experience, being associated with the environment data, wherein the user content is associated with the first content,
    determine, based on a difference between the initial emotional state and the first emotional state of the user, a second content being associated with the user content and being associated with the first content,
    provide the second content to the user,
    measure, in response to providing the second content to the user, second user body data of the user and determine, based on the measured second user body data, a second emotional state of the user, and
    refine, based on a difference between the first emotional state and the second emotional and a difference between the initial emotional state and the second emotional state, the second content provided to the user for increasing the difference between the initial emotional state and the second emotional state of the user.

(2) The information processing circuitry of (1), wherein the information processing circuitry is configured to, if the initial emotional state and the first emotional state of the user are the same, determine and provide a different first content being associated with the abstract content to the user.

(3) The information processing circuitry of (1) or (2), wherein the information processing circuitry is configured to provide visual content inside the cabin to the user as part of the provided content.

(4) The information processing circuitry of anyone of (1) to (3), wherein the information processing circuitry is configured to provide audio content inside the cabin to the user as part of the provided content.

(5) The information processing circuitry of anyone of (1) to (4), wherein the information processing circuitry is configured to provide smell content inside the cabin to the user as part of the provided content.

(6) The information processing circuitry of anyone of (1) to (5), wherein the information processing circuitry is configured to provide haptic content to the user as part of the provided content.

(7) The information processing circuitry of anyone of (1) to (6), wherein the information processing device includes a user body sensor unit configured to measure the user body data, wherein the user body sensor unit includes at least one of a heart rate sensor, a blood pressure sensor, a body temperature sensor, a respiration rate sensor, a sweat sensor, and a camera.

(8) The information processing circuitry of (7), wherein the user body sensor unit includes a brain-machine-interface attached to the user.

(9) The information processing circuitry of anyone of (1) to (8), wherein the information processing circuitry is further configured to:
  obtain user actions from the user;
  acquire abstract content data and user content data being associated with at least one of a date and an obtained first user action of the user; and
  determine the emotional state of the user further based on an obtained second user action.

(10) The information processing circuitry of (9), wherein the information processing circuitry is further configured to trigger acquiring of the abstract content data in response to at least one of random acquisition trigger, a date and an obtained third user action of the user.

(11) An information processing method for controlling a content provided to a user inside a cabin of an autonomous vehicle, including:
  obtaining environment data;
  acquiring abstract content data, representing abstract content, being associated with the obtained environment data;
  measuring initial user body data of the user and determining, based on the measured initial user body data, an initial emotional state of the user;
  determining and providing a first content, being associated with the abstract content, to the user;
  measuring, in response to providing the first content to the user, first user body data of the user and determining, based on the measured first user body data, a first emotional state of the user; and
  if the initial emotional state and the first emotional state of the user are different:
    acquiring user content data from a database, representing user content associated with a past user experience, being associated with the environment data, wherein the user content is associated with the first content,
    determining, based on a difference between the initial emotional state and the first emotional state of the user, a second content being associated with the user content and being associated with the first content, providing the second content to the user,
  measuring, in response to providing the second content to the user, second user body data of the user and determine, based on the measured second user body data, a second emotional state of the user, and
  refining, based on a difference between the first emotional state and the second emotional and a difference between the initial emotional state and the second emotional state, the second content provided to the user for increasing the difference between the initial emotional state and the second emotional state of the user.

(12) The information processing method of (11), further including:
  determining and providing, if the initial emotional state and the first emotional state of the user are the same, a different first content being associated with the abstract content to the user.

(13) The information processing method of (11) or (12), further including: providing visual content inside the cabin to the user as part of the provided content.

(14) The information processing method of anyone of (11) to (13), further including:
  providing audio content inside the cabin to the user as part of the provided content.

(15) The information processing method of anyone of (11) to (14), further including:
  providing smell content inside the cabin to the user as part of the provided content.

(16) The information processing method of anyone of (11) to (15), further including:
  providing haptic content to the user as part of the provided content.

(17) The information processing method of anyone of (11) to (16), further including:
  measuring the user body data by at least one of a heart rate sensor, a blood pressure sensor, a body temperature sensor, a respiration rate sensor, a sweat sensor, and a camera.

(18) The information processing method of (17), further including:
  measuring the user body data further by a brain-machine-interface attached to the user.

(19) The information processing method of anyone of (11) to (18), further including:
  obtaining user actions from the user;
  acquiring abstract content data and user content data being associated with at least one of a date and an obtained first user action of the user; and
  determining the emotional state of the user further based on an obtained second user action.

(20) The information processing method of (19), further including:
  triggering acquiring of the abstract content data in response to at least one of random acquisition trigger, a date and an obtained third user action of the user.

(21) A computer program comprising program code causing a computer to perform the method according to anyone of (11) to (20), when being carried out on a computer.

(22) A non-transitory computer-readable recording medium that stores therein a computer program product, which, when executed by a processor, causes the method according to anyone of (11) to (20) to be performed.

(23) The information processing circuitry of anyone of (1) to (10), further configured to determine content with a machine learning algorithm.

(24) The information processing method of anyone of (11) to (20), further including determining content with a machine learning algorithm.

The invention claimed is:
1. An autonomous vehicle, comprising:
  a vehicle state detecting unit including at least one of:
    a gyro sensor configured to detect an angular velocity of axial rotational movement of a body of the autonomous vehicle,
    an acceleration sensor configured to detect an acceleration of the autonomous vehicle, or
    sensors configured to detect an amount of operation of an accelerator pedal, an amount of operation of a brake pedal, a steering angle of a steering wheel, an engine speed, or a rotational speed of wheels of the autonomous vehicle,
  a driving system control processing circuitry configured to perform arithmetic processing using a signal input from the vehicle state detecting unit and control at least one of an internal combustion engine, a driving motor, an electric power steering device, or a brake device of the autonomous vehicle based upon the arithmetic processing,
  a body system control processing circuitry configured to control at least one of a keyless entry system, a smart key system, a power window device, or various kinds of lamps including a headlamp, a backup lamp, a brake lamp, a turn signal, and a fog lamp,
  a battery control processing circuitry configured to control a secondary battery, which is a power supply source for the driving motor, based upon at least one of a battery temperature, a battery output voltage, or an amount of remaining charge,
  an outside-vehicle information detecting section including at least one of an ultrasonic sensor, a radar device, or a LIDAR device,
  an outside-vehicle information detecting processing circuitry configured to detect information about the outside of the autonomous vehicle based upon a signal input from the outside-vehicle information detecting section,
  a user body sensor configured to measure user body data of a user inside a cabin of the autonomous vehicle and including at least one of a heart rate sensor, a blood pressure sensor, a body temperature sensor, a respiration rate sensor, a sweat sensor, or a camera,
  an in-vehicle information detecting processing circuitry configured to detect information about the inside of the autonomous vehicle based upon a signal input from the user body sensor,
  an air conditioner,
  a smell content providing unit including a plurality of containers including predetermined substances having a particular smell,
  a speaker inside the cabin of the autonomous vehicle configured to provide audio content,
  a haptic actuator inside the cabin of the autonomous vehicle configured to provide haptic content,
  an integrated control processing circuitry; and
  a communication network connecting each of the driving system control processing circuitry, the body system control processing circuitry, the battery control processing circuitry, the outside-vehicle information detecting processing circuitry, the in-vehicle information detecting processing circuitry, and the integrated control processing circuitry, wherein the integrated control processing circuitry is configured to:
obtain environment data from at least one of the outside-vehicle information detecting processing circuitry or the in-vehicle information detecting processing circuitry;
acquire abstract content data, representing abstract content, being associated with the obtained environment data;
control the user body sensor to measure initial user body data of the user;
determine, based on the measured initial user body data, an initial emotional state of the user;
determine and provide a first content, being associated with the abstract content, to the user;
control the user body sensor to measure, in response to providing the first content to the user, first user body data of the user;
determine, based on the measured first user body data, a first emotional state of the user;
if the initial emotional state of the user and the first emotional state of the user are the same, determine and provide a different first content being associated with the abstract content to the user; and
if the initial emotional state of the user and the first emotional state of the user are different:
acquire user content data from a database, representing user content associated with a past user experience, being associated with the environment data, wherein the user content is associated with the first content,
determine, based on a difference between the initial emotional state of the user and the first emotional state of the user, a second content being associated with the user content and being associated with the first content,
provide the second content to the user,
control the user body sensor to measure, in response to providing the second content to the user, second user body data of the user,
determine, based on the measured second user body data, a second emotional state of the user, and
refine, based on a difference between the first emotional state of the user and the second emotional state of the user and a difference between the initial emotional state of the user and the second emotional state of the user, the second content provided to the user for increasing the difference between the initial emotional state of the user and the second emotional state of the user, and
wherein refining the second content includes at least one of controlling the speaker inside the cabin of the autonomous vehicle to provide audio content to the user inside the cabin, controlling the air conditioner to change a temperature inside the cabin, controlling the smell content providing unit to release at least one of the predetermined inside the cabin of the autonomous vehicle to provide smell content to the user inside the cabin, or controlling the haptic actuator inside the cabin of the autonomous vehicle to provide haptic content to the user inside the cabin.

2. The autonomous vehicle according to claim 1, wherein the integrated control processing circuitry is configured to provide visual content inside the cabin to the user as part of the provided content.

3. The autonomous vehicle according to claim 1, wherein refining the second content includes controlling the speaker to provide the audio content to the user inside the cabin.

4. The autonomous vehicle according to claim 1, wherein refining the second content includes controlling the smell content providing unit to release the at least one of the predetermined substances to provide the smell content to the user inside the cabin.

5. The autonomous vehicle according to claim 1, wherein refining the second content includes controlling the haptic actuator to provide the haptic content to the user inside the cabin.

6. The autonomous vehicle according to claim 1, wherein the user body sensor includes a brain-machine-interface attached to the user.

7. The autonomous vehicle according claim 1, wherein the integrated control processing circuitry is further configured to:
obtain user actions from the user;
acquire the abstract content data and the user content data being associated with at least one of a date and an obtained first user action of the user; and
determine the emotional state of the user further based on an obtained second user action.

8. The autonomous vehicle according to claim 7, wherein the integrated control processing circuitry is further configured to trigger acquiring of the abstract content data in response to at least one of a random acquisition trigger, a date, or an obtained third user action of the user.

9. A method for an autonomous vehicle, the method comprising:
detecting at least one of:
an angular velocity of axial rotational movement of a body of the autonomous vehicle using a gyro sensor,
an acceleration of the autonomous vehicle using an acceleration sensor, or
an amount of operation of an accelerator pedal, an amount of operation of a brake pedal, a steering angle of a steering wheel, an engine speed, or a rotational speed of wheels of the autonomous vehicle using sensors,
performing arithmetic processing based upon the detecting;
controlling at least one of an internal combustion engine, a driving motor, an electric power steering device, or a brake device of the autonomous vehicle based upon the arithmetic processing
controlling at least one of a keyless entry system, a smart key system, a power window device, or various kinds of lamps including a headlamp, a backup lamp, a brake lamp, a turn signal, and a fog lamp,
controlling a secondary battery, which is a power supply source for the driving motor, based upon at least one of a battery temperature, a battery output voltage, or an amount of remaining charge,
detecting information about the outside of the autonomous vehicle based upon a signal input from an outside-vehicle information detecting section including at least one of an ultrasonic sensor, a radar device, or a LIDAR device,
detecting information about the inside of the autonomous vehicle based upon a signal input from a user body sensor configured to measure user body data of a user inside a cabin of the autonomous vehicle and including at least one of a heart rate sensor, a blood pressure sensor, a body temperature sensor, a respiration rate sensor, a sweat sensor, or a camera, obtaining environment data from at least one of the information about the outside of the autonomous vehicle or the information about the inside of the autonomous vehicle;

acquiring abstract content data, representing abstract content, being associated with the obtained environment data;

controlling the user body sensor to measure initial user body data of the user;

determining, based on the measured initial user body data, an initial emotional state of the user;

determining and providing a first content, being associated with the abstract content, to the user;

controlling the user body sensor to measure, in response to providing the first content to the user, first user body data of the user;

determining, based on the measured first user body data, a first emotional state of the user;

if the initial emotional state of the user and the first emotional state of the user are the same determining and providing a different first content being associated with the abstract content to the user; and if the initial emotional state of the user and the first emotional state of the user are different:

acquiring user content data from a database, representing user content associated with a past user experience, being associated with the environment data, wherein the user content is associated with the first content, determining, based on a difference between the initial emotional state of the user and the first emotional state of the user, a second content being associated with the user content and being associated with the first content, providing the second content to the user, control the user body sensor to measure, in response to providing the second content to the user, second user body data of the user, determine, based on the measured second user body data, a second emotional state of the user, and refining, based on a difference between the first emotional state of the user and the second emotional state of the user and a difference between the initial emotional state of the user and the second emotional state of the user, the second content provided to the user for increasing the difference between the initial emotional state of the user and the second emotional state of the user, wherein refining the second content includes at least one of controlling a speaker inside the cabin of the autonomous vehicle to provide audio content to the user inside the cabin, controlling an air conditioner to change a temperature inside the cabin, controlling a smell content providing unit including a plurality of containers including predetermined substances having a particular smell to release at least one of the predetermined substances inside the cabin of the autonomous vehicle to provide smell content to the user inside the cabin, or controlling a haptic actuator inside the cabin of the autonomous vehicle to provide haptic content to the user inside the cabin.

10. The method according to claim 9, further comprising:
providing visual content inside the cabin to the user as part of the provided content.

11. The method according to claim 9, wherein refining the second content includes controlling the speaker to provide the audio content to the user inside the cabin.

12. The method according to claim 9, wherein refining the second content includes controlling the smell content providing unit to release the at least one of the predetermined substances to provide the smell content to the user inside the cabin.

13. The method according to claim 9, wherein refining the second content includes controlling the haptic actuator to provide the haptic content to the user inside the cabin.

14. The method according to claim 9, further comprising:
measuring the user body data further by a brain-machine-interface attached to the user.

15. The method according to claim 9, further comprising:
obtaining user actions from the user;
acquiring the abstract content data and the user content data being associated with at least one of a date and an obtained first user action of the user; and
determining the emotional state of the user further based on an obtained second user action.

16. The method according to claim 15, further comprising:
triggering acquiring of the abstract content data in response to at least one of a random acquisition trigger, a date, or an obtained third user action of the user.

17. The autonomous vehicle according to claim 1, wherein refining the second content includes controlling the air conditioner to change the temperature inside the cabin.

18. The method according to claim 9, wherein refining the second content includes controlling the air conditioner to change the temperature inside the cabin.

* * * * *